US012672883B2

(12) United States Patent
Read et al.

(10) Patent No.: US 12,672,883 B2
(45) Date of Patent: Jul. 7, 2026

(54) ORTHOPEDIC RASP AND SURGICAL TECHNIQUE FOR PREPARING AN INTERCUNEIFORM JOINT FOR FUSION

(71) Applicant: Treace Medical Concepts, Inc., Ponte Vedra, FL (US)

(72) Inventors: Mitch Read, Berlin, MA (US); Adriaan Kuyler, Ponte Vedra, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 109 days.

(21) Appl. No.: 18/435,912

(22) Filed: Feb. 7, 2024

(65) Prior Publication Data

US 2024/0260976 A1 Aug. 8, 2024

Related U.S. Application Data

(60) Provisional application No. 63/444,224, filed on Feb. 8, 2023.

(51) Int. Cl.
A61B 17/16 (2006.01)
A61F 2/46 (2006.01)
(Continued)

(52) U.S. Cl.
CPC ........ A61B 17/1682 (2013.01); A61F 2/4606 (2013.01); A61B 2017/564 (2013.01);
(Continued)

(58) Field of Classification Search
CPC ............ A61B 17/1735; A61B 17/1739; A61B 17/1775; A61B 17/8061
See application file for complete search history.

(56) References Cited

U.S. PATENT DOCUMENTS 3,584,667 A 6/1971 Reiland
3,664,022 A 5/1972 Small
(Continued)

FOREIGN PATENT DOCUMENTS

AU 2009227957 B2 7/2014
CA 2491824 A1 9/2005
(Continued)

OTHER PUBLICATIONS

Sokoloff, "Lapidus Procedure," Textbook of Bunion Surgery, Chapter 15, 1981, pp. 277-287.
(Continued)

*Primary Examiner* — Anu Ramana
(74) *Attorney, Agent, or Firm* — Fredrikson & Byron, P.A.

(57) ABSTRACT

Orthopedic rasps and associated techniques can be used for preparing an intercuneiform joint for fusion. In some examples, the orthopedic rasp includes a body having a length extending from a first end to a second end and defining a first widthwise surface and a second widthwise surface opposite the first widthwise surface. The rasp may include a rasp head having a plurality of cutting teeth extending outwardly from one or both of the first widthwise surface and the second widthwise surface of the body. The plurality of cutting teeth may be spaced apart from each other along the width and/or length of the body. The rasp head can be configured to be inserted into an intercuneiform joint space between a first cuneiform and a second cuneiform.

18 Claims, 11 Drawing Sheets

(51) Int. Cl.

| | |
|---|---|
| *A61B 17/56* | (2006.01) |
| *A61B 90/00* | (2016.01) |
| *A61F 2/30* | (2006.01) |

(52) U.S. Cl.

CPC .................. *A61B 2090/062* (2016.02); *A61F 2002/30622* (2013.01)

(56) References Cited

U.S. PATENT DOCUMENTS

| | | | |
|---|---|---|---|
| 3,835,858 | A | 9/1974 | Hagen |
| D234,214 | S | 1/1975 | Mcevoy |
| 4,069,824 | A | 1/1978 | Weinstock |
| 4,159,716 | A | 7/1979 | Borchers |
| 4,187,840 | A | 2/1980 | Watanabe |
| D258,932 | S | 4/1981 | Graham |
| 4,335,715 | A | 6/1982 | Kirkley |
| 4,338,927 | A | 7/1982 | Volkov et al. |
| 4,349,018 | A | 9/1982 | Chambers |
| 4,364,381 | A | 12/1982 | Sher et al. |
| 4,409,973 | A | 10/1983 | Neufeld |
| 4,440,168 | A | 4/1984 | Warren |
| 4,501,268 | A | 2/1985 | Comparetto |
| 4,502,474 | A | 3/1985 | Comparetto |
| 4,509,511 | A | 4/1985 | Neufeld |
| 4,565,191 | A | 1/1986 | Slocum |
| 4,570,624 | A | 2/1986 | Wu |
| 4,598,447 | A * | 7/1986 | Whyde .................. B23D 71/00 |
| | | | 407/29.1 |
| 4,601,290 | A | 7/1986 | Effron et al. |
| 4,625,725 | A * | 12/1986 | Davison ............. A61B 17/1659 |
| | | | 407/29.1 |
| 4,627,425 | A | 12/1986 | Reese |
| 4,628,919 | A | 12/1986 | Clyburn |
| 4,632,102 | A | 12/1986 | Comparetto |
| 4,664,102 | A | 5/1987 | Comparetto |
| 4,708,133 | A | 11/1987 | Comparetto |
| 4,736,737 | A | 4/1988 | Fargie et al. |
| 4,750,481 | A | 6/1988 | Reese |
| 4,754,746 | A | 7/1988 | Cox |
| 4,757,810 | A | 7/1988 | Reese |
| 4,895,141 | A | 1/1990 | Koeneman et al. |
| 4,952,214 | A | 8/1990 | Comparetto |
| 4,959,066 | A | 9/1990 | Dunn et al. |
| D312,954 | S | 12/1990 | Wilbanks |
| 4,978,347 | A | 12/1990 | Ilizarov |
| 4,988,349 | A | 1/1991 | Pennig |
| 4,995,875 | A | 2/1991 | Coes |
| 5,021,056 | A | 6/1991 | Hofmann et al. |
| 5,035,698 | A | 7/1991 | Comparetto |
| 5,042,983 | A | 8/1991 | Rayhack |
| 5,049,149 | A | 9/1991 | Schmidt |
| 5,053,039 | A | 10/1991 | Hofmann et al. |
| 5,078,719 | A | 1/1992 | Schreiber |
| 5,112,334 | A | 5/1992 | Alchermes et al. |
| 5,147,364 | A | 9/1992 | Comparetto |
| 5,176,685 | A | 1/1993 | Rayhack |
| 5,207,676 | A | 5/1993 | Canadell et al. |
| 5,246,444 | A | 9/1993 | Schreiber |
| D340,634 | S | 10/1993 | Lipic |
| 5,254,119 | A | 10/1993 | Schreiber |
| 5,312,412 | A | 5/1994 | Whipple |
| 5,358,504 | A | 10/1994 | Paley et al. |
| 5,364,402 | A | 11/1994 | Mumme et al. |
| 5,374,271 | A | 12/1994 | Hwang |
| 5,413,579 | A | 5/1995 | Du |
| 5,417,694 | A | 5/1995 | Marik et al. |
| 5,449,360 | A | 9/1995 | Schreiber |
| 5,454,815 | A | 10/1995 | Geisser et al. |
| 5,470,335 | A | 11/1995 | Du Toit |
| 5,490,854 | A | 2/1996 | Fisher et al. |
| 5,529,075 | A | 6/1996 | Clark |
| 5,540,695 | A | 7/1996 | Levy |
| 5,578,038 | A | 11/1996 | Slocum |
| 5,586,564 | A | 12/1996 | Barrett et al. |
| 5,601,565 | A | 2/1997 | Huebner |
| 5,613,969 | A | 3/1997 | Jenkins, Jr. |
| 5,620,442 | A | 4/1997 | Bailey et al. |
| 5,620,448 | A | 4/1997 | Puddu |
| 5,643,270 | A | 7/1997 | Combs |
| 5,667,510 | A | 9/1997 | Combs |
| H1706 | H | 1/1998 | Mason |
| 5,722,978 | A | 3/1998 | Jenkins, Jr. |
| 5,749,875 | A | 5/1998 | Puddu |
| 5,779,709 | A | 7/1998 | Harris, Jr. et al. |
| 5,788,695 | A | 8/1998 | Richardson |
| 5,803,924 | A | 9/1998 | Oni et al. |
| 5,810,822 | A | 9/1998 | Mortier |
| 5,843,085 | A | 12/1998 | Graser |
| 5,857,995 | A | 1/1999 | Thomas et al. |
| D405,178 | S | 2/1999 | Dykes |
| 5,893,553 | A | 4/1999 | Pinkous |
| 5,911,724 | A | 6/1999 | Wehrli |
| 5,935,128 | A | 8/1999 | Carter et al. |
| 5,941,877 | A | 8/1999 | Viegas et al. |
| 5,951,556 | A | 9/1999 | Faccioli et al. |
| 5,980,526 | A | 11/1999 | Johnson et al. |
| 5,984,931 | A | 11/1999 | Greenfield |
| 6,007,535 | A | 12/1999 | Rayhack et al. |
| 6,027,504 | A | 2/2000 | Mcguire |
| 6,030,391 | A | 2/2000 | Brainard et al. |
| 6,056,764 | A | 5/2000 | Smith |
| 6,139,559 | A | 10/2000 | Nordan et al. |
| 6,162,223 | A | 12/2000 | Orsak et al. |
| 6,171,309 | B1 | 1/2001 | Huebner |
| 6,203,545 | B1 | 3/2001 | Stoffella |
| 6,248,109 | B1 | 6/2001 | Stoffella |
| 6,391,031 | B1 | 5/2002 | Toomey |
| 6,416,465 | B2 | 7/2002 | Brau |
| 6,478,799 | B1 | 11/2002 | Williamson |
| 6,511,481 | B2 | 1/2003 | Von Hoffmann et al. |
| 6,547,793 | B1 | 4/2003 | Mcguire |
| 6,676,662 | B1 | 1/2004 | Bagga et al. |
| D487,559 | S | 3/2004 | Callander |
| 6,719,773 | B1 | 4/2004 | Boucher et al. |
| 6,743,233 | B1 | 6/2004 | Baldwin et al. |
| 6,755,838 | B2 | 6/2004 | Trnka |
| 6,796,986 | B2 | 9/2004 | Duffner |
| 6,859,661 | B2 | 2/2005 | Tuke |
| 6,964,645 | B1 | 11/2005 | Smits |
| 7,018,383 | B2 | 3/2006 | Mcguire |
| 7,033,361 | B2 | 4/2006 | Collazo |
| 7,097,647 | B2 | 8/2006 | Segler |
| 7,112,204 | B2 | 9/2006 | Justin et al. |
| 7,153,310 | B2 | 12/2006 | Ralph et al. |
| D535,747 | S | 1/2007 | Isogimi |
| 7,182,766 | B1 | 2/2007 | Mogul |
| 7,241,298 | B2 | 7/2007 | Nemec et al. |
| 7,282,054 | B2 | 10/2007 | Steffensmeier et al. |
| 7,377,924 | B2 | 5/2008 | Raistrick et al. |
| D575,128 | S | 8/2008 | Clampitt, Jr. et al. |
| 7,465,303 | B2 | 12/2008 | Riccione et al. |
| 7,540,874 | B2 | 6/2009 | Trumble et al. |
| 7,572,258 | B2 * | 8/2009 | Stiemborg ............. A61B 17/15 |
| | | | 606/79 |
| 7,572,260 | B1 | 8/2009 | Nelson |
| 7,641,660 | B2 | 1/2010 | Lakin et al. |
| D610,257 | S | 2/2010 | Horton |
| 7,686,811 | B2 | 3/2010 | Byrd et al. |
| 7,691,108 | B2 | 4/2010 | Lavallee |
| 7,763,026 | B2 | 7/2010 | Egger et al. |
| D629,900 | S | 12/2010 | Fisher |
| D639,631 | S | 6/2011 | Kempker et al. |
| 7,967,823 | B2 | 6/2011 | Ammann et al. |
| 7,972,338 | B2 | 7/2011 | O'Brien |
| 8,021,364 | B2 | 9/2011 | Nolde |
| D646,389 | S | 10/2011 | Claypool et al. |
| 8,057,478 | B2 | 11/2011 | Kuczynski et al. |
| 8,062,301 | B2 | 11/2011 | Ammann et al. |
| D651,315 | S | 12/2011 | Bertoni et al. |
| D651,316 | S | 12/2011 | May et al. |
| 8,080,010 | B2 | 12/2011 | Schulz et al. |
| 8,080,045 | B2 | 12/2011 | Wotton, III |
| 8,083,746 | B2 | 12/2011 | Novak |

(56) References Cited

U.S. PATENT DOCUMENTS

| | | | |
|---|---|---|---|
| 8,123,753 B2 | 2/2012 | Poncet | |
| 8,137,406 B2 | 3/2012 | Novak et al. | |
| 8,147,530 B2 | 4/2012 | Strnad et al. | |
| 8,167,918 B2 | 5/2012 | Strnad et al. | |
| 8,172,848 B2 | 5/2012 | Tomko et al. | |
| 8,192,441 B2 | 6/2012 | Collazo | |
| 8,197,487 B2 | 6/2012 | Poncet et al. | |
| 8,231,623 B1 | 7/2012 | Jordan | |
| 8,231,663 B2 | 7/2012 | Kay et al. | |
| 8,236,000 B2 | 8/2012 | Ammann et al. | |
| 8,246,561 B1 | 8/2012 | Agee et al. | |
| D666,721 S | 9/2012 | Wright et al. | |
| 8,262,664 B2 | 9/2012 | Justin et al. | |
| 8,277,459 B2 | 10/2012 | Sand et al. | |
| 8,282,644 B2 | 10/2012 | Edwards | |
| 8,282,645 B2 | 10/2012 | Lawrence et al. | |
| 8,292,966 B2 | 10/2012 | Morton | |
| 8,303,596 B2 | 11/2012 | Plaky et al. | |
| 8,313,492 B2 | 11/2012 | Wong et al. | |
| 8,323,289 B2 | 12/2012 | Re | |
| 8,337,503 B2 | 12/2012 | Lian | |
| 8,343,159 B2 | 1/2013 | Bennett | |
| 8,377,105 B2 | 2/2013 | Bscher | |
| D679,395 S | 4/2013 | Wright et al. | |
| D679,397 S | 4/2013 | Packard et al. | |
| 8,409,209 B2 | 4/2013 | Ammann et al. | |
| 8,435,246 B2 | 5/2013 | Fisher et al. | |
| 8,475,462 B2 | 7/2013 | Thomas et al. | |
| 8,486,076 B2 | 7/2013 | Chavarria et al. | |
| 8,496,662 B2 | 7/2013 | Novak et al. | |
| 8,518,045 B2 | 8/2013 | Szanto | |
| 8,523,870 B2 | 9/2013 | Green, II et al. | |
| 8,529,571 B2 | 9/2013 | Horan et al. | |
| 8,540,777 B2 | 9/2013 | Ammann et al. | |
| 8,545,508 B2 | 10/2013 | Collazo | |
| D694,884 S | 12/2013 | Mooradian et al. | |
| D695,402 S | 12/2013 | Dacosta et al. | |
| 8,652,142 B2 | 2/2014 | Geissler | |
| 8,657,820 B2 | 2/2014 | Kubiak et al. | |
| D701,303 S | 3/2014 | Cook | |
| 8,672,945 B2 | 3/2014 | Lavallee et al. | |
| 8,696,716 B2 | 4/2014 | Kartalian et al. | |
| 8,702,715 B2 | 4/2014 | Ammann et al. | |
| D705,929 S | 5/2014 | Frey | |
| 8,715,363 B2 | 5/2014 | Ratron et al. | |
| 8,728,084 B2 | 5/2014 | Berelsman et al. | |
| 8,758,354 B2 | 6/2014 | Habegger et al. | |
| 8,764,760 B2 | 7/2014 | Metzger et al. | |
| 8,764,763 B2 | 7/2014 | Wong et al. | |
| 8,771,279 B2 | 7/2014 | Philippon et al. | |
| 8,777,948 B2 | 7/2014 | Bernsteiner | |
| 8,784,427 B2 | 7/2014 | Fallin et al. | |
| 8,784,457 B2 | 7/2014 | Graham | |
| 8,795,286 B2 | 8/2014 | Sand et al. | |
| 8,801,727 B2 | 8/2014 | Chan et al. | |
| 8,808,303 B2 | 8/2014 | Stemniski et al. | |
| 8,828,012 B2 | 9/2014 | May et al. | |
| 8,858,602 B2 | 10/2014 | Weiner et al. | |
| 8,870,875 B2 | 10/2014 | Romagnoli et al. | |
| 8,882,778 B2 | 11/2014 | Ranft | |
| 8,882,816 B2 | 11/2014 | Kartalian et al. | |
| 8,888,785 B2 | 11/2014 | Ammann et al. | |
| D720,456 S | 12/2014 | Dacosta et al. | |
| 8,900,247 B2 | 12/2014 | Tseng et al. | |
| 8,906,026 B2 | 12/2014 | Ammann et al. | |
| 8,945,132 B2 | 2/2015 | Play et al. | |
| 8,998,903 B2 | 4/2015 | Price et al. | |
| 8,998,904 B2 | 4/2015 | Zeetser et al. | |
| 9,011,507 B2 | 4/2015 | Schelling | |
| D728,352 S | 5/2015 | Martinson | |
| 9,023,052 B2 | 5/2015 | Lietz et al. | |
| 9,044,250 B2 | 6/2015 | Olsen et al. | |
| 9,060,822 B2 | 6/2015 | Wright et al. | |
| 9,089,376 B2 | 7/2015 | Medoff et al. | |
| 9,101,421 B2 | 8/2015 | Blacklidge | |
| 9,107,715 B2 | 8/2015 | Blitz et al. | |
| 9,113,920 B2 | 8/2015 | Ammann et al. | |
| D740,424 S | 10/2015 | Dacosta et al. | |
| D765,844 S | 9/2016 | Dacosta | |
| D766,434 S | 9/2016 | Dacosta | |
| D766,437 S | 9/2016 | Dacosta | |
| D766,438 S | 9/2016 | Dacosta | |
| D766,439 S | 9/2016 | Dacosta | |
| 9,452,057 B2 | 9/2016 | Dacosta et al. | |
| 9,522,023 B2 | 12/2016 | Haddad et al. | |
| 9,592,084 B2 * | 3/2017 | Grant | A61B 17/864 |
| 9,750,538 B2 | 9/2017 | Soffiatti et al. | |
| 9,775,628 B2 | 10/2017 | Monaghan | |
| 9,785,747 B2 | 10/2017 | Geebelen | |
| 9,936,994 B2 | 4/2018 | Smith et al. | |
| 9,980,760 B2 | 5/2018 | Dacosta et al. | |
| 10,028,750 B2 | 7/2018 | Rose | |
| 10,064,631 B2 | 9/2018 | Dacosta et al. | |
| 10,159,499 B2 | 12/2018 | Dacosta et al. | |
| 10,292,713 B2 | 5/2019 | Fallin et al. | |
| 10,327,829 B2 | 6/2019 | Dacosta et al. | |
| 10,335,220 B2 | 7/2019 | Smith et al. | |
| 10,376,268 B2 | 8/2019 | Fallin et al. | |
| 10,470,779 B2 | 11/2019 | Fallin et al. | |
| 10,779,867 B2 | 9/2020 | Penzimer et al. | |
| 10,786,292 B2 * | 9/2020 | Singh | A61B 17/8057 |
| 10,856,886 B2 | 12/2020 | Dacosta et al. | |
| 10,856,918 B2 | 12/2020 | Dacosta | |
| D911,799 S | 3/2021 | Sweitzer et al. | |
| 10,939,939 B1 | 3/2021 | Gil et al. | |
| 11,083,622 B2 | 8/2021 | Cady et al. | |
| 11,304,705 B2 | 4/2022 | Fallin et al. | |
| 11,571,312 B1 | 2/2023 | Parekh et al. | |
| 12,396,770 B2 * | 8/2025 | McAleer | A61B 17/8866 |
| 12,408,965 B2 * | 9/2025 | Sayger | A61B 17/8897 |
| 2002/0058944 A1 | 5/2002 | Michelson | |
| 2002/0099381 A1 | 7/2002 | Maroney | |
| 2002/0107519 A1 | 8/2002 | Dixon et al. | |
| 2002/0165552 A1 | 11/2002 | Duffner | |
| 2002/0198531 A1 | 12/2002 | Millard et al. | |
| 2004/0010259 A1 | 1/2004 | Keller et al. | |
| 2004/0039394 A1 | 2/2004 | Conti et al. | |
| 2004/0097946 A1 | 5/2004 | Dietzel et al. | |
| 2004/0138669 A1 | 7/2004 | Horn | |
| 2005/0004587 A1 | 1/2005 | Matsutani et al. | |
| 2005/0004676 A1 | 1/2005 | Schon et al. | |
| 2005/0059978 A1 | 3/2005 | Sherry et al. | |
| 2005/0070909 A1 | 3/2005 | Egger et al. | |
| 2005/0075641 A1 | 4/2005 | Singhatat et al. | |
| 2005/0101961 A1 | 5/2005 | Huebner et al. | |
| 2005/0149042 A1 | 7/2005 | Metzger | |
| 2005/0228389 A1 | 10/2005 | Stiernborg | |
| 2005/0251147 A1 | 11/2005 | Novak | |
| 2005/0267482 A1 | 12/2005 | Hyde | |
| 2005/0273112 A1 | 12/2005 | Mcnamara | |
| 2006/0036257 A1 | 2/2006 | Steffensmeier | |
| 2006/0058824 A1 | 3/2006 | Kozlowski | |
| 2006/0089650 A1 * | 4/2006 | Nolde | A61B 17/1684 606/85 |
| 2006/0129163 A1 | 6/2006 | Mcguire | |
| 2006/0206044 A1 | 9/2006 | Simon | |
| 2006/0217733 A1 | 9/2006 | Plassky et al. | |
| 2006/0229621 A1 | 10/2006 | Cadmus | |
| 2006/0241607 A1 | 10/2006 | Myerson et al. | |
| 2006/0241608 A1 | 10/2006 | Myerson et al. | |
| 2006/0264961 A1 | 11/2006 | Murray-Brown | |
| 2007/0010818 A1 | 1/2007 | Stone et al. | |
| 2007/0123857 A1 | 5/2007 | Deffenbaugh et al. | |
| 2007/0233138 A1 | 10/2007 | Figueroa et al. | |
| 2007/0265634 A1 | 11/2007 | Weinstein | |
| 2007/0276383 A1 | 11/2007 | Rayhack | |
| 2008/0009863 A1 | 1/2008 | Bond et al. | |
| 2008/0015603 A1 | 1/2008 | Collazo | |
| 2008/0039850 A1 | 2/2008 | Rowley et al. | |
| 2008/0091197 A1 | 4/2008 | Coughlin | |
| 2008/0140081 A1 | 6/2008 | Heavener et al. | |
| 2008/0147073 A1 | 6/2008 | Ammann et al. | |
| 2008/0172054 A1 | 7/2008 | Claypool et al. | |
| 2008/0195215 A1 | 8/2008 | Morton | |

(56) References Cited

U.S. PATENT DOCUMENTS

| | | |
|---|---|---|
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0112212 A1 | 4/2009 | Murray et al. |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2009/0306675 A1 | 12/2009 | Wong et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0217328 A1 | 8/2010 | Terrill et al. |
| 2010/0234849 A1 | 9/2010 | Bouadi |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0144676 A1 | 6/2011 | Yamaguchi et al. |
| 2011/0178524 A1 | 7/2011 | Lawrence et al. |
| 2011/0245835 A1 | 10/2011 | Dodds et al. |
| 2011/0264149 A1 | 10/2011 | Pappalardo et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Wright et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Anderson et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0135956 A1 | 5/2016 | Kulber |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0338697 A1 | 11/2016 | Biedermann et al. |
| 2016/0354127 A1 | 12/2016 | Lundquist et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0056031 A1 | 3/2017 | Awtrey et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2018/0132868 A1 | 5/2018 | Dacosta et al. |
| 2018/0289379 A1 | 10/2018 | Dacosta et al. |
| 2018/0344334 A1 | 12/2018 | Kim et al. |

(56) References Cited

U.S. PATENT DOCUMENTS

| | | | |
|---|---|---|---|
| 2019/0336140 A1 | 11/2019 | Dacosta et al. | |
| 2020/0015865 A1 | 1/2020 | Lamm et al. | |
| 2020/0015874 A1 | 1/2020 | Hartson et al. | |
| 2020/0046377 A1 | 2/2020 | Woodard et al. | |
| 2020/0229828 A1 | 7/2020 | Wagner et al. | |
| 2020/0237387 A1 | 7/2020 | Luttrell et al. | |
| 2020/0330109 A1 | 10/2020 | Woodard et al. | |
| 2021/0015527 A1* | 1/2021 | Singh | A61B 17/8061 |
| 2021/0077192 A1 | 3/2021 | Perler et al. | |
| 2022/0257267 A1 | 8/2022 | Decarbo et al. | |
| 2022/0323085 A1 | 10/2022 | Hales et al. | |
| 2022/0338934 A1 | 10/2022 | Perler et al. | |
| 2022/0409222 A1 | 12/2022 | Cundiff et al. | |
| 2023/0142406 A1 | 5/2023 | Amiot et al. | |
| 2023/0149031 A1 | 5/2023 | Woodard et al. | |
| 2023/0201543 A1 | 6/2023 | Simopoulos | |
| 2023/0255651 A1 | 8/2023 | Cundiff et al. | |
| 2023/0263540 A1 | 8/2023 | Dayton et al. | |

FOREIGN PATENT DOCUMENTS

| | | | |
|---|---|---|---|
| CA | 2854997 A1 | 5/2013 | |
| CH | 695846 A5 | 9/2006 | |
| CN | 2930668 Y | 8/2007 | |
| CN | 201558162 U | 8/2010 | |
| CN | 201572172 U | 9/2010 | |
| CN | 201586060 U | 9/2010 | |
| CN | 201912210 U | 8/2011 | |
| CN | 101237835 B | 11/2012 | |
| CN | 202801773 U | 3/2013 | |
| CN | 103462675 A | 12/2013 | |
| CN | 103505276 A | 1/2014 | |
| CN | 203458450 U | 3/2014 | |
| CN | 103735306 A | 4/2014 | |
| CN | 102860860 B | 5/2014 | |
| CN | 203576647 U | 5/2014 | |
| CN | 104490460 A | 4/2015 | |
| CN | 104510523 A | 4/2015 | |
| CN | 104523327 A | 4/2015 | |
| CN | 104546102 A | 4/2015 | |
| CN | 204379413 U | 6/2015 | |
| CN | 204410951 U | 6/2015 | |
| CN | 204428143 U | 7/2015 | |
| CN | 204428144 U | 7/2015 | |
| CN | 204428145 U | 7/2015 | |
| CN | 204446081 U | 7/2015 | |
| DE | 202006010241 U1 | 3/2007 | |
| DE | 102007053058 B3 | 4/2009 | |
| EP | 685206 B1 | 9/2000 | |
| EP | 1508316 B1 | 5/2007 | |
| EP | 1897509 B1 | 7/2009 | |
| EP | 2124772 A1 | 12/2009 | |
| EP | 2124832 B1 | 8/2012 | |
| EP | 2632349 A1 | 9/2013 | |
| EP | 2665428 A1 | 11/2013 | |
| EP | 2742878 A1 | 6/2014 | |
| EP | 2750617 A1 | 7/2014 | |
| EP | 2849684 A1 | 3/2015 | |
| EP | 2624764 B1 | 12/2015 | |
| EP | 3023068 A2 | 5/2016 | |
| FR | 2362616 A1 | 3/1978 | |
| FR | 2764183 B1 | 11/1999 | |
| FR | 2953120 B1 | 1/2012 | |
| FR | 3030221 A1 | 6/2016 | |
| GB | 231718 A | 4/1925 | |
| GB | 2154143 A | 9/1985 | |
| GB | 2154144 A | 9/1985 | |
| GB | 2334214 B | 1/2003 | |
| IN | 200904479 P2 | 5/2010 | |
| IN | 140DELNP2012 A | 1/2013 | |
| IN | 201302004 P2 | 1/2013 | |
| JP | 63005739 A | 1/1988 | |
| JP | 05031116 A | 2/1993 | |
| JP | 2004174265 A | 6/2004 | |
| JP | 2006158972 A | 6/2006 | |

| | | | |
|---|---|---|---|
| JP | 4134243 B2 | 8/2008 | |
| JP | 2008537498 A | 9/2008 | |
| JP | 4162380 B2 | 10/2008 | |
| JP | 2011092405 A | 5/2011 | |
| JP | 2011523889 A | 8/2011 | |
| JP | 4796943 B2 | 10/2011 | |
| JP | 5466647 B2 | 4/2014 | |
| JP | 2014511207 A | 5/2014 | |
| JP | 2014521384 A | 8/2014 | |
| JP | 5628875 B2 | 11/2014 | |
| KR | 100904142 B1 | 6/2009 | |
| MD | 756 B1 | 7/1997 | |
| RU | 2098036 C1 | 12/1997 | |
| RU | 2195892 C2 | 1/2003 | |
| RU | 2320287 C1 | 3/2008 | |
| RU | 2321366 C2 | 4/2008 | |
| RU | 2321369 C1 | 4/2008 | |
| RU | 2346663 C2 | 2/2009 | |
| RU | 2412662 C1 | 2/2011 | |
| SU | 1333328 A2 | 8/1987 | |
| WO | 0166022 A1 | 9/2001 | |
| WO | 03075775 A1 | 9/2003 | |
| WO | 2004089227 A2 | 10/2004 | |
| WO | 2008051064 A1 | 5/2008 | |
| WO | 2008097781 A1 | 8/2008 | |
| WO | 2009029798 A1 | 3/2009 | |
| WO | 2009032101 A2 | 3/2009 | |
| WO | 2009158522 A1 | 12/2009 | |
| WO | 2011037885 A1 | 3/2011 | |
| WO | 2012029008 A1 | 3/2012 | |
| WO | 2012058344 A1 | 5/2012 | |
| WO | 2012099612 A1 | 7/2012 | |
| WO | 2013090392 A1 | 6/2013 | |
| WO | 2013134387 A1 | 9/2013 | |
| WO | 2013169475 A1 | 11/2013 | |
| WO | 2014020561 A1 | 2/2014 | |
| WO | 2014022055 A1 | 2/2014 | |
| WO | 2014035991 A1 | 3/2014 | |
| WO | 2014085882 A1 | 6/2014 | |
| WO | 2014147099 A1 | 9/2014 | |
| WO | 2014152219 A2 | 9/2014 | |
| WO | 2014152535 A1 | 9/2014 | |
| WO | 2014177783 A1 | 11/2014 | |
| WO | 2014200017 A1 | 12/2014 | |
| WO | 2015094409 A1 | 6/2015 | |
| WO | 2015105880 A1 | 7/2015 | |
| WO | 2015127515 A2 | 9/2015 | |
| WO | 2016134160 A1 | 8/2016 | |
| WO | 2020180598 A1 | 9/2020 | |

OTHER PUBLICATIONS

Talbot et al., "Assessing Sesamoid Subluxation: How Good is the AP Radiograph?," Foot and Ankle International, vol. 19, No. 8, Aug. 1998, pp. 547-554.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Weber et al., "A Simple System For Navigation of Bone Alignment Osteotomies of The Tibia," International Congress Series, vol. 1268, Jan. 2004, pp. 608-613, (Abstract Only).

Wukich et al., "Hypermobility of the First Tarsometatarsal Joint," Foot and Ankle Clinics, vol. 10, No. 1, Mar. 2005, pp. 157-166.

Stahl et al., "Derotation of Post-Traumatic Femoral Deformities By Closed Intramedullary Sawing," Injury, vol. 37, No. 2, Feb. 2006, pp. 145-151, (Abstract Only).

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

(56)          References Cited

OTHER PUBLICATIONS

Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).

Mtek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Mtek, "Neue Techniken in der Fuchirurgie Das V-tek-System," ABW Wissenschaftsverlag GmbH, 2009, 11 pages, including English Abstract.

Stamatis et al., "Mini Locking Plate as Medial Buttress for Oblique Osteotomy for Hallux Valgus," Foot & Ankle International, vol. 31, No. 10, Oct. 2010, pp. 920-922.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Shurnas et al., "Proximal Metatarsal Opening Wedge Osteotomy," Operative Techniques in Foot and Ankle Surgery, Section I, Chapter 13, 2011, pp. 73-78.

Weil et al., "Anatomic Plantar Plate Repair Using the Weil Metatarsal Osteotomy Approach," Foot & Ankle Specialist, vol. 4, No. 3, 2011, pp. 145-150.

Wienke et al., "Bone Stimulation For Nonunions: What the Evidence Reveals," Podiatry Today, vol. 24, No. 9, Sep. 2011, pp. 52-57.

Tricot et al., "3D-corrective osteotomy using surgical guides for posttraumatic distal humeral deformity," Acta Orthopaedica Belgica, vol. 78, No. 4, 2012, pp. 538-542.

TempFix Spanning the Ankle Joint Half Pin and Transfixing Pin Techniques, Biomet Orthopedics, Surgical Technique, 2012, 16 pages.

Siddiqui et al. "Fixation of Metatarsal Fracture With Bone Plate in a Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Small Bone External Fixation System, Acumed, Surgical Technique, Effective date Sep. 2014, 8 pages.

Stableloc External Fixation System, Acumed, Product Overview, Effective date Sep. 2015, 4 pages.

Yasuda et al., "Proximal Supination Osteotomy of the First Metatarsal for Hallux Valgus," Foot and Ankle International, vol. 36, No. 6, Jun. 2015, pp. 696-704.

Patil et al. "Radiological Biometric Study of Metatarsals and Phalanges" Journal of Clinical and Diagnostic Research, Published Sep. 1, 2017, pp. 2.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

Internatioanl Searching Authority "International Search Report and Written Opinion" From Applicatoin No. PCT/US2024/14839, Mailed Aug. 8, 2024, pp. 12.

Use for BME Speed Nitinol Staple Fixation for the Lapidus Procedure, "date unknown, 1 page."

Lapidus, "The Author's Bunion Operation From 1931 to 1959," Clinical Orthopaedics, vol. 16, 1960, pp. 119-135.

Hardy et al., "Observations on Hallux Valgus," The Journal of Bone and Joint Surgery, vol. 33B, No. 3, Aug. 1951,pp. 376-391.

Mizuno et al., "Detorsion Osteotomy of the First Metatarsal Bone in Hallux Valgus," Japanese Orthopaedic Association, Tokyo, 1956; 30:813-819.

Odenbring et al., "A guide instrument for high tibial osteotomy," Acta Orthopaedica Scandinavica, vol. 60, No. 4, 1989, pp. 449-451.

Myerson, "Cuneiform-Metatarsal Arthrodesis," The Foot and Ankle, Chapter 9, 1997, pp. 107-117.

Schon et al., "Cuneiform-Metatarsal Arthrodesis for Hallux Valgus," The Foot and Ankle, Second Edition, Chapter 8, 2002, pp. 99-117.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Hetherington et al., "Evaluation of surgical experience and the use of an osteotomy guide on the apical angle of an Austin osteotomy," The Foot, vol. 18, 2008, pp. 159-164.

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Magin, "Computernavigierter Gelenkersatz am Knie mit dem Orthopilot," Operative Orthopdie und Traumatologie, vol. 22, No. 1, 2010, pp. 63-80, including English Abstract on p. 64.

Moore et al., "Effect of Ankle Flexion Angle on Axial Alignment of Total Ankle Replacement," Foot and Ankle International, vol. 31, No. 12, Dec. 2010, pp. 1093-1098, (Abstract Only).

MiniRail System, Small Bone Innovations, Surgical Technique, 2010, 24 pages.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Le et al., "Tarsometatarsal Arthrodesis," Operative Techniques in Foot and Ankle Surgery, Section II, Chapter 40, 2011, pp. 281-285.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Integra, "Integra Large Qwix Positioning and Fixation Screw," Surgical Technique," 2012, 16 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.

(56) References Cited

OTHER PUBLICATIONS

Mortier et al., "Axial Rotation of the First Metatarsal Head in a Normal Population and Hallux Valgus Patients," Orthopaedics and Traumatology: Surgery and Research, vol. 98, 2012, pp. 677-683.

Modular Rail System: External Fixator, Smith & Nephew, Surgical Technique, 2013, 44 pages.

Otsuki et al., "Developing a novel custom cutting guide for curved per-acetabular osteotomy," International Orthopaedics (SICOT), vol. 37, 2013, pp. 1033-1038.

Peters et al., "Flexor Hallucis Longus Tendon Laceration as a Complication of Total Ankle Arthroplasty," Foot & Ankle International, vol. 34, No. 1, 2013, pp. 148-149.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Groves, "Operative Report," St. Tammany Parish Hospital, Date of Procedure, Mar. 26, 2014, 2 pages.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.

Mini Joint Distractor, Arthrex, retrieved Dec. 19, 2014, from the Internet: <http://www.arthrex.com/foot-ankle/mini-joint-distractor/products>, 2 pages.

Nagy et al., "The AO Ulnar Shortening Osteotomy System Indications and Surgical Technique," Journal of Wrist Surgery, vol. 3, No. 2, 2014, pp. 91-97.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Rx-Fix Mini Rail External Fixator, Wright Medical Technology, Brochure, Aug. 15, 2014, 2 pages.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

Hatch et al., "Triplane Hallux Abducto Valgus Classification," The Journal of Foot & Ankle Surgery, vol. 57, No. 5, Sep./Oct. 2018, published online: May 18, 2018, pp. 972-981.

Lopez et al., "Metatarsalgia: Assessment Algorithm and Decision Making," Foot and Ankle Clinics, vol. 24, No. 4, Dec. 2019, published online: Sep. 25, 2019, pp. 561-569.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Michelangelo Bunion System, Surgical Technique, Instratek Incorporated, publication date unknown, 4 pages.

Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.

D'amico et al., "Motion of the First Ray: Clarification Through Investigation," Journal of the American Podiatry Association, vol. 69, No. 1, Jan. 1979, pp. 17-23.

Alvine et al., "Peg and Dowel Fusion of the Proximal Interphalangeal Joint," Foot & Ankle, vol. 1, No. 2, 1980, pp. 90-94.

Dayton et al., "Biwinged Excision for Round Pedal Lesions," The Journal of Foot and Ankle Surgery, vol. 35, No. 3, 1996, pp. 244-249.

Coughlin, "Fixation of the Lapidus Arthrodesis with a Plantar Interfragmentary Screw and Medial Low Profile Locking Plate," Orthopaedics and Traumatology, vol. 7, 1999, pp. 133-143.

Blomer, "Knieendoprothetik—Herstellerische Probleme und technologische Entwicklungen," Orthopade, vol. 29, 2000, pp. 688-696, including English Abstract on p. 689.

Bednarz et al., "Modified Lapidus Procedure for the Treatment of Hypermobile Hallux Valgus," Foot & Ankle International, vol. 21, No. 10, Oct. 2000, pp. 816-821.

"Patient to Patient Precision, Accu-Cut, Osteotomy Guide System," BioPro, Foot & Ankle International Journal, vol. 23, No. 8, Aug. 2002, 2 pages.

Anderson et al., "Uncemented STAR Total Ankle Prostheses," The Journal of Bone and Joint Surgery, vol. 86(1, Suppl 2), Sep. 2004, pp. 103-111, (Abstract Only).

Coetzee et al., "The Lapidus Procedure: A Prospective Cohort Outcome Study," Foot & Ankle International, vol. 25, No. 8, Aug. 2004, pp. 526-531.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

Lag Screw Target Bow, Stryker Leibinger GmbH & Co. KG, Germany 2004, 8 pages.

Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.

Hoffmann II Compact External Fixation System, Stryker, Brochure, Literature No. 5075-1-500, 2006, 12 pages.

"Futura Forefoot Implant Arthroplasty Products," Tornier, Inc., 2008, 14 pages.

Hoffmann II Micro Lengthener, Stryker, Operative Technique, Literature No. 5075-2-002, 2008, 12 pages.

"Lapidus Pearls: Gaining Joint Exposure to Decrease Non-Union," Youtube, Retrieved online from <https://www.youtube.com/watch?v =-jqJyE7pj-Y>, dated Nov. 2, 2009, 3 pages.

"Visionaire: Patient Matched Cutting Blocks Surgical Procedure," Smith & Nephew, Inc., 2009, 2 pages.

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Bouaicha et al., "Fixation of Maximal Shift Scarf Osteotomy with Inside-Out Plating: Technique Tip," Foot & Ankle International, vol. 32, No. 5, May 2011, pp. 567-569.

Coetzee et al., "Revision Hallux Valgus Correction," Operative Techniques in Foot and Ankle Surgery, Section I, Chapter 15, 2011, pp. 84-96.

Dayton et al., "A User-Friendly Method of Pin Site Management for External Fixators," Foot and Ankle Specialist, Sep. 16, 2011, 4 pages.

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

(56)                  References Cited

OTHER PUBLICATIONS

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
"Prophecy Inbone Preoperative Navigation Guides," Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
"Foot and Ankle Instrument Set," Smith & Nephew, 2013, 2 pages.
"Speed Continuous Active Compression Implant," BioMedical Enterprises, Inc., A120-029 Rev. 3, 2013, 4 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Bauer et al., "Offset-V Osteotomy of the First Metatarsal Shaft in Hallux Abducto Valgus," McGlamrys Comprehensive Textbook of Foot and Ankle Surgery, Fourth Edition, vol. 1, Chapter 29, 2013, 26 pages.
Collan et al., "The biomechanics of the first metatarsal bone in hallux valgus: A preliminary study utilizing a weight bearing extremity CT," Foot and Ankle Surgery, vol. 19, 2013, pp. 155-161.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
"Acumed Osteotomiesystem Operationstechnik," Acumed, 2014, 19 pages (including 3 pages English translation).
"HAT-TRICK Lesser Toe Repair System, Foot and Ankle Technique Guide, Metatarsal Shortening Osteotomy Surgical Technique," Smith & Nephew, 2014, 16 pages.
"Smith & Nephew scores a HAT-TRICK with its entry into the high-growth hammer toe repair market," Smith & Nephew, Jul. 31, 2014, 2 pages.
Catanese et al., "Measuring Sesamoid Position in Hallux Valgus: When Is the Sesamoid Axial View Necessary," Foot and Ankle Specialist, 2014, 3 pages.
Dayton et al., "Clarification of the Anatomic Definition of the Bunion Deformity," The Journal of Foot and Ankle Surgery, vol. 53, 2014, pp. 160-163.
HAT-TRICK Lesser Toe Repair System, Smith & Nephew, Brochure, Aug. 2014, 12 pages.
Hoffmann Small System External Fixator Orthopedic Instruments, Stryker, retrieved Dec. 19, 2014, from the Internet: <http://www.alibaba.com/product-detail/Stryker-Hoffmann-Small-System-External-Fixator_1438850129.html>, 3 pages.
"Reconstructive Surgery of the Foot & Ankle," The Podiatry Institute, Update 2015, Conference Program, May 2015, 28 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
"Accu-Cut Osteotomy Guide System," BioPro, Brochure, Oct. 2018, 2 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.

Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
Eustace et al., "Hallux valgus, first metatarsal pronation and collapse of the medial longitudinal arch—a radiological correlation," Skeletal Radiology, vol. 23, 1994, pp. 191-194.
Dayton et al., "Medial Incision Approach to the First Metatarsophalangeal Joint," The Journal of Foot and Ankle Surgery, vol. 40, No. 6, Nov./Dec. 2001, pp. 414-417.
Gotte, "Entwicklung eines Assistenzrobotersystems fr die Knieendoprothetik," Forschungsberichte, Technische Universitat Munchen, 165, 2002, 11 pages, including partial English Translation.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Garthwait, "Accu-Cut System Facilitates Enhanced Precision," Podiatry Today, vol. 18, No. 6, Jun. 2005, 6 pages.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Gerard et al., "The Modified Lapidus Procedure," Orthopedics, vol. 31, No. 3, Mar. 2008, 7 pages.
Easley et al., "What is the Best Treatment for Hallux Valgus?," Evidence-Based Orthopaedics—The Best Answers to Clinical Questions, Chapter 73, 2009, pp. 479-491.
Dayton et al., "The Extended Knee Hemilithotomy Position for Gastrocnemius Recession," The Journal of Foot and Ankle Surgery, vol. 49, 2010, pp. 214-216.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Fleming et al., "Results of Modified Lapidus Arthrodesis Procedure Using Medial Eminence as an Interpositional Autograft," The Journal of Foot & Ankle Surgery, vol. 50, 2011, pp. 272-275.

(56) References Cited

OTHER PUBLICATIONS

Giannoudis et al., "Hallux Valgus Correction," Practical Procedures in Elective Orthopaedic Surgery, Pelvis and Lower Extremity, Chapter 38, 2012, 22 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Principles of Management of Growth Plate Fractures in the Foot and Ankle," Clinics in Podiatric Medicine and Surgery, Pediatric Foot Deformities, Oct. 2013, 17 pages.

Decarbo et al., "Resurfacing Interpositional Arthroplasty for Degenerative Joint Disease of the First Metatarsalphalangeal Joint," Podiatry Management, Jan. 2013, pp. 137-142.

Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Dayton et al., "Technique for Minimally Invasive Reduction of Calcaneal Fractures Using Small Bilateral External Fixation," The Journal of Foot and Ankle Surgery, Article in Press, 2014, 7 pages.

Decarbo et al., "Locking Plates: Do They Prevent Complications?," Podiatry Today, Apr. 2014, 7 pages.

Decarbo et al., "The Weil Osteotomy: A Refresher," Techniques in Foot and Ankle Surgery, vol. 13, No. 4, Dec. 2014, pp. 191-198.

Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Fishco, "Making the Lapidus Easy," The Podiatry Institute, Update 2014, Chapter 14, 2014, pp. 91-93.

Dayton et al., "A new triplanar paradigm for bunion management," Lower Extremity Review, Apr. 2015, 9 pages.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

Fallin et al., US Provisional Application Entitled Indexed Tri-Planar Osteotomy Guide and Method, U.S. Appl. No. 62/118,378, filed Feb. 19, 2015, 62 pages.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

Groves, "Functional Position Joint Sectioning: Pre-Load Method for Lapidus Arthrodesis," The Podiatry Institute, Update 2015, Chapter 6, 2015, pp. 23-29.

* cited by examiner

ACCESS TMT JOINT     250

PREPARE METATARSAL AND CUNEIFORM     252

MOVE METATARSAL     254

COMPRESS BONES     256

APPLY FIXATION     258

ORTHOPEDIC RASP AND SURGICAL TECHNIQUE FOR PREPARING AN INTERCUNEIFORM JOINT FOR FUSION

RELATED APPLICATION

This application claims the benefit of U.S. Provisional Application Ser. No. 63/444,224, filed Feb. 8, 2023, the entire contents of which are incorporated herein by reference.

TECHNICAL FIELD

This disclosure relates to surgical instruments and, more particularly, to rasp instruments and related surgical techniques for preparing small bones for fusion.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

Another type of bone deformity in the foot is metatarsus adductus. MTA is a deformity of the foot in which the metatarsals are angulated into adduction. MTA is typically characterized by a medial deviation of the metatarsals in the transverse plane. For example, MTA is often described as a structural deformity occurring at the Lisfranc joint (tarsometatarsal joints), with the metatarsals being deviated medially with reference to the lesser tarsus.

In some cases, surgical intervention is needed to address hallux valgus and/or MTA deformities. Surgical intervention may involve realigning one or more bones of the foot, improving patient comfort and increasing patient mobility. A clinician may use a variety of different surgical instruments and techniques during a surgical procedure performed on the foot, including one or more instruments to prepare bones for fusing together following completion of the surgical procedure. Surgical instruments and techniques that can facilitate efficient, accurate, and reproducible clinical results are useful for practitioners performing bone correction and realignment techniques.

SUMMARY

In general, this disclosure generally relates to orthopedic rasp instruments and associated systems (e.g., kits) as well as surgical techniques utilizing an orthopedic rasp. In particular, the disclosure relates to orthopedic rasp instruments and techniques for preparing an intercuneiform joint space for fusion. In some examples according to the disclosure, an orthopedic rasp can be inserted into an intercuneiform joint space between a first cuneiform and a second cuneiform. The rasp can then be used to prepare a surface of the first cuneiform and an opposed surface of the second cuneiform for fusion. For example, the rasp can include teeth on one or both sides of the instrument that, when the instrument is moved relative to the bones, causes the teeth to cut into the bones to provide bleeding bone surfaces. The prepared surfaces of the two bones can be compressed together and held in a fixed position using a fixation device for fusion during which natural bone growth causes the prepared surfaces to fuse together across the intercuneiform joint space.

While a rasp according to the disclosure can have a variety of different configurations, the rasp may be configured specifically for preparation of opposed bones defining the intercuneiform joint space. For example, the rasp may have a body defining a length and first and second widthwise surfaces opposite each other. The rasp can have multiple cutting teeth extending outward from one side of the rasp (one widthwise surface) or both sides of the rasp (both widthwise surfaces). For example, the rasp may have cutting teeth extending outwardly from both sides of the rasp to allow simultaneous preparation of a surface of the first cuneiform and an opposed surface of the second cuneiform and/or to help ensure that the surfaces of the two cuneiforms prepared by the rasp are aligned with each other across the intercuneiform joint space.

Independent of the number or configuration of the cutting teeth on the rasp, the rasp may be sized and shaped for insertion into the intercuneiform joint space. For example, the rasp may have a rasp head having a thickness within a range from 0.8 mm to 1.5 mm, a width within a range from 4 mm to 6 mm, and a length within a range from 15 mm to 30 mm. A rasp with comparatively small dimensions configured for insertion into the intercuneiform joint space may facilitate accurate and reproducible fusion across the intercuneiform joint space while helping the clinician avoid cutting or otherwise damaging soft tissue (e.g., tendons, ligaments) over or adjacent the intercuneiform joint space. Further, a rasp with comparatively small dimensions configured for insertion into the intercuneiform joint space can allow the clinician to prepare and fuse the first cuneiform and the second cuneiform over a comparatively small surface area, e.g., providing precisely directed spot bone preparation and fusion, avoiding preparation of larger areas of bone causing greater bone damage and requiring greater healing. Providing comparatively small, precisely directed spot bone preparation and fusion using a rasp instrument and/or surgical technique according to the disclosure can be using during a minimally invasive procedure (among other use cases), where access to the intercuneiform joint space is made through a comparatively small incision.

Instruments and techniques according to the disclosure may be used in a procedure in which only the first cuneiform and second cuneiform are prepared and the intercuneiform joint fixated for fusion without performing surgical techniques on other bones or joints. In practice, an intercuneiform joint fusion may typically be performed in conjunction with a metatarsal realignment procedure, such as a metatarsal realignment procedure to treat a bunion deformity. During a metatarsal realignment procedure, a metatarsal separated from the first cuneiform by a tarsometatarsal joint may be moved to help correct a misalignment of the metatarsal. The end of the first cuneiform facing the tarsometatarsal joint and the end of the metatarsal facing the tarsometatarsal joint may each be prepared (e.g., by cutting the end of one or both bones). Before or after preparing one or both bone ends, the metatarsal can be moved in one or more planes (e.g., a transverse plane, a frontal plane, and/or a sagittal plane). A fixation device can be applied across the tarsometatarsal joint that fixates the moved position of the metatarsal while the ends of the first cuneiform and metatarsal fuse across the tarsometatarsal joint.

Preparation of the first cuneiform and second cuneiform across the intercuneiform joint space for fusion using a rasp may be performed to help address transverse plane splay and/or instability at the intercuneiform joint notwithstanding the correction and fixation applied at the tarsometatarsal joint. For example, after moving the metatarsal relative to the first cuneiform and applying one or more fixation device across the tarsometatarsal joint, a patient may exhibit laxity at the first cuneiform-second cuneiform joint. This can allow the intermetatarsal angle between the metatarsal being realigned and an adjacent metatarsal to open up at the intercuneiform joint. For these and/or other reasons, a clinician may prepare the intercuneiform joint for fusion using a rasp and apply a fixation device (e.g., crossing screw) across the first cuneiform and the second cuneiform. The fixation and subsequent fusion can stabilize the intercuneiform joint as part of a wholistic correction procedure.

In one example, a method of preparing an intercuneiform joint for fusion is described. The method involves inserting an orthopedic rasp into an intercuneiform joint between a first cuneiform and a second cuneiform. The orthopedic rasp includes a body defining a first widthwise surface and a second widthwise surface opposite the first widthwise surface and a rasp head defined along at least a portion of a length of the body. In some examples, the rasp head includes a first plurality of cutting teeth extending outwardly from the first widthwise surface of the body and a second plurality of cutting teeth extending outwardly from the second widthwise surface of the body. The example method also involves moving the orthopedic rasp relative to the first cuneiform and the second cuneiform, thereby causing the first plurality of cutting teeth to prepare a surface of the first cuneiform and the second plurality of cutting teeth to prepare an opposed surface of the second cuneiform across the intercuneiform joint. The example method also involves applying a fixation device to the first cuneiform and the second cuneiform and across the intercuneiform joint. The fixation device can hold the surface of the first cuneiform prepared by the first plurality of cutting teeth in contact with the opposed surface of the second cuneiform prepared by the second plurality of cutting teeth for fusion.

In another example, an orthopedic rasp for preparing an intercuneiform joint for fusion is described. The rasp includes a body having a length extending from a first end to a second end and defining a first widthwise surface and a second widthwise surface opposite the first widthwise surface. The rasp also includes a rasp head defined along at least a portion of the length of the body. The rasp head includes a plurality of cutting teeth extending outwardly from one or both of the first widthwise surface and the second widthwise surface of the body. The example specifies that at least some of the plurality of cutting teeth are spaced apart from each other along the length of the body and that the rasp head is configured to be inserted into an intercuneiform joint space between a first cuneiform and a second cuneiform.

The details of one or more examples are set forth in the accompanying drawings and the description below. Other features, objects, and advantages will be apparent from the description and drawings, and from the claims.

DETAILED DESCRIPTION

Figure 1A:
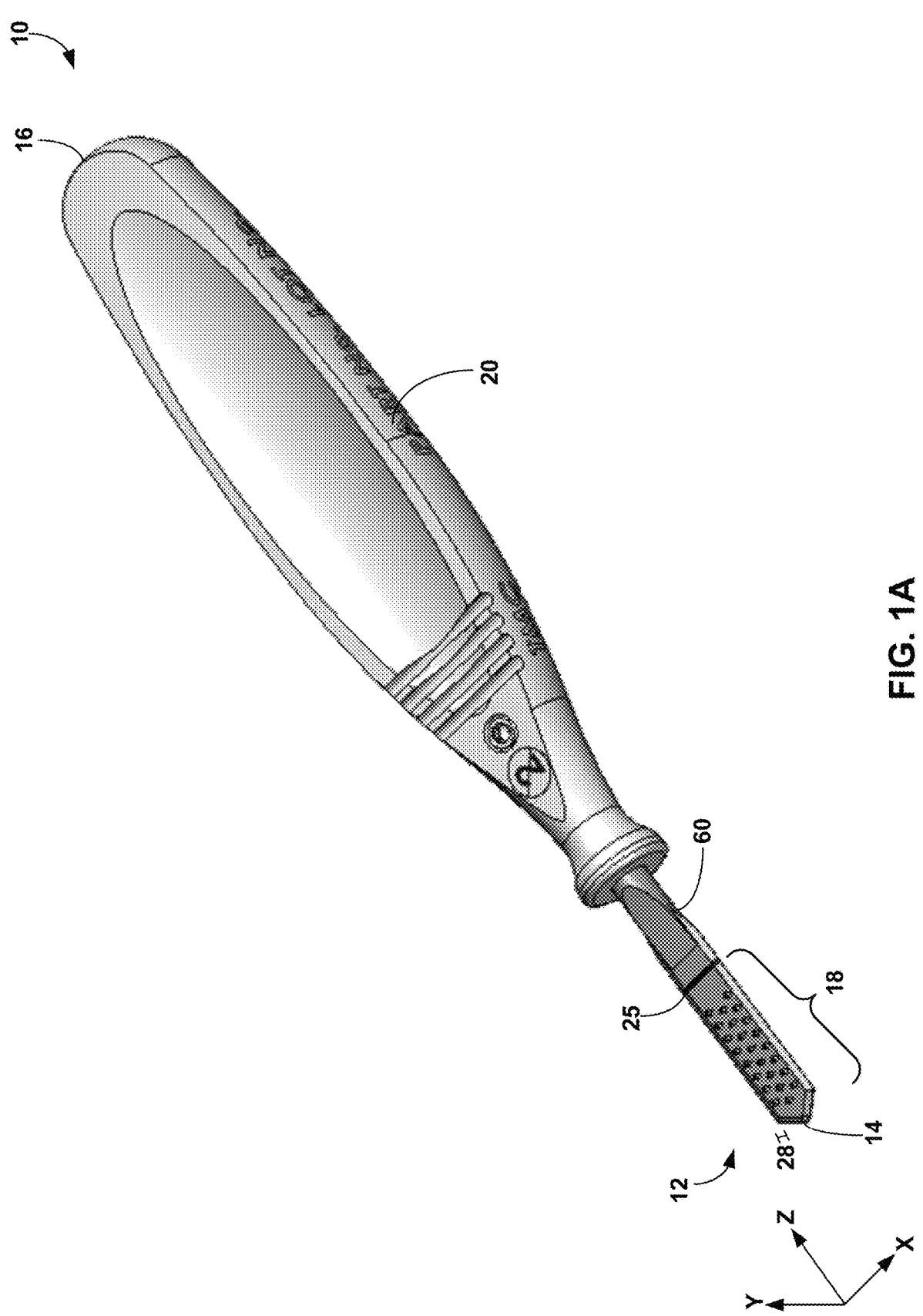
FIGS. 1A-1C are different views of an example orthopedic rasp according to the disclosure.

This disclosure generally relates to orthopedic rasp instruments and surgical techniques utilizing rasps to prepare an intercuneiform joint space between a first cuneiform and a second cuneiform for fusion. In some examples, the rasp is configured (e.g., sized and shaped) to be inserted into an intercuneiform joint space between a medial cuneiform and an adjacent intermediate cuneiform. One or more cutting faces of the rasp can be moved relative to a lateral side of the medial cuneiform and a medial side of the intermediate cuneiform, e.g., forming bleeding bone surfaces that are aligned with each other and that contact each other when the medial cuneiform and the intermediate cuneiform are compressed together and the intercuneiform joint space closed. While the rasp may find particular utility preparing the joint space between medial cuneiform and the intermediate cuneiform for fusion, the instrument may be used to prepare the joint space between intermediate cuneiform and the lateral cuneiform for fusion, and/or the joint space between lateral cuneiform and the cuboid for fusion.

In exemplary applications, the devices, systems, and techniques can be used during a surgical procedure performed on one or more bones, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing devices and/or techniques of the disclosure can be used in conjunction with a procedure to correct an alignment between a metatarsal (e.g. a first metatarsal) and a cuneiform (e.g., a medial cuneiform), such as a bunion correction. An example of such a procedure is a lapidus procedure. In another example, the devices, systems, and/or techniques can be utilized in conjunction with a procedure to modify a position of one portion of a bone relative to another portion of the same bone. An example of such a procedure is an osteotomy procedure (e.g., metatarsal osteotomy procedure) in which the bone is cut into at least two different bones and one portion (e.g., a distal portion) is realigned relative to another bone portion (e.g., a proximal portion) of the same bone.

Preparation and fusion of one or more intercuneiform joints is performed as a standalone procedure or in conjunction with preparation and fusion of one or more TMT joints. Preparation and fusion of a TMT joint may be performed to treat metatarsus adductus, hallux valgus, arthritis, and/or other bone and/or joint conditions.

Metatarsus adductus is a deformity of the foot characterized by a transverse plane deformity where the metatarsals are adducted at the Lisfranc joint. The extent of a metatarsus adductus deformity can be characterized by a metatarsus adductus angle. The metatarsus adductus angle can be defined as the angle between the longitudinal axis of the second metatarsal (representing the longitudinal axis of the metatarsus) and the longitudinal axis of the lesser tarsus. The measurement of the longitudinal axis of the lesser tarsus can be characterized by a line perpendicular to the transverse axis of the lesser tarsus using the lateral joint of the fourth metatarsal with the cuboid as a reference.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux adductus angle, the angle between the long axes of the first metatarsal and proximal phalanx in the transverse plane. An increase in the hallux adductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the crista of the first metatarsal head.

Preparation and fusion of an intercuneiform joint may facilitate corrective alignment of a metatarsal relative to an opposed cuneiform and/or relative to an adjacent metatarsal. For example, preparation and fusion of an intercuneiform joint may help reduce or eliminate splay of a metatarsal (e.g., first metatarsal) in which the distal end of the metatarsal shifts medially outwardly from an adjacent metatarsal, enlarging an intermetatarsal angle between the two metatarsal. Additionally or alternatively, preparation and fusion of an intercuneiform joint may help stabilize an unstable joint.

While techniques and devices are generally described herein in connection with the intercuneiform joint between the medial cuneiform and the intermediate cuneiform, the techniques and devices may be used on other adjacent bones (e.g., separated from each other by a joint). For example, devices and techniques may be used for preparation and fusion of an intercuneiform joint between the intermediate cuneiform and the lateral cuneiform and/or the joint between the lateral cuneiform and cuboid. Accordingly, reference to particular bones may be replaced with other bone pairs as described herein.

The anatomy of the foot and example techniques utilizing an orthopedic rasp according to the disclosure will be described in greater detail with respect to FIGS. 4-9. However, an example orthopedic rasp according to the disclosure will first be described with respect to FIGS. 1-3.

Figures 1B, 1C:
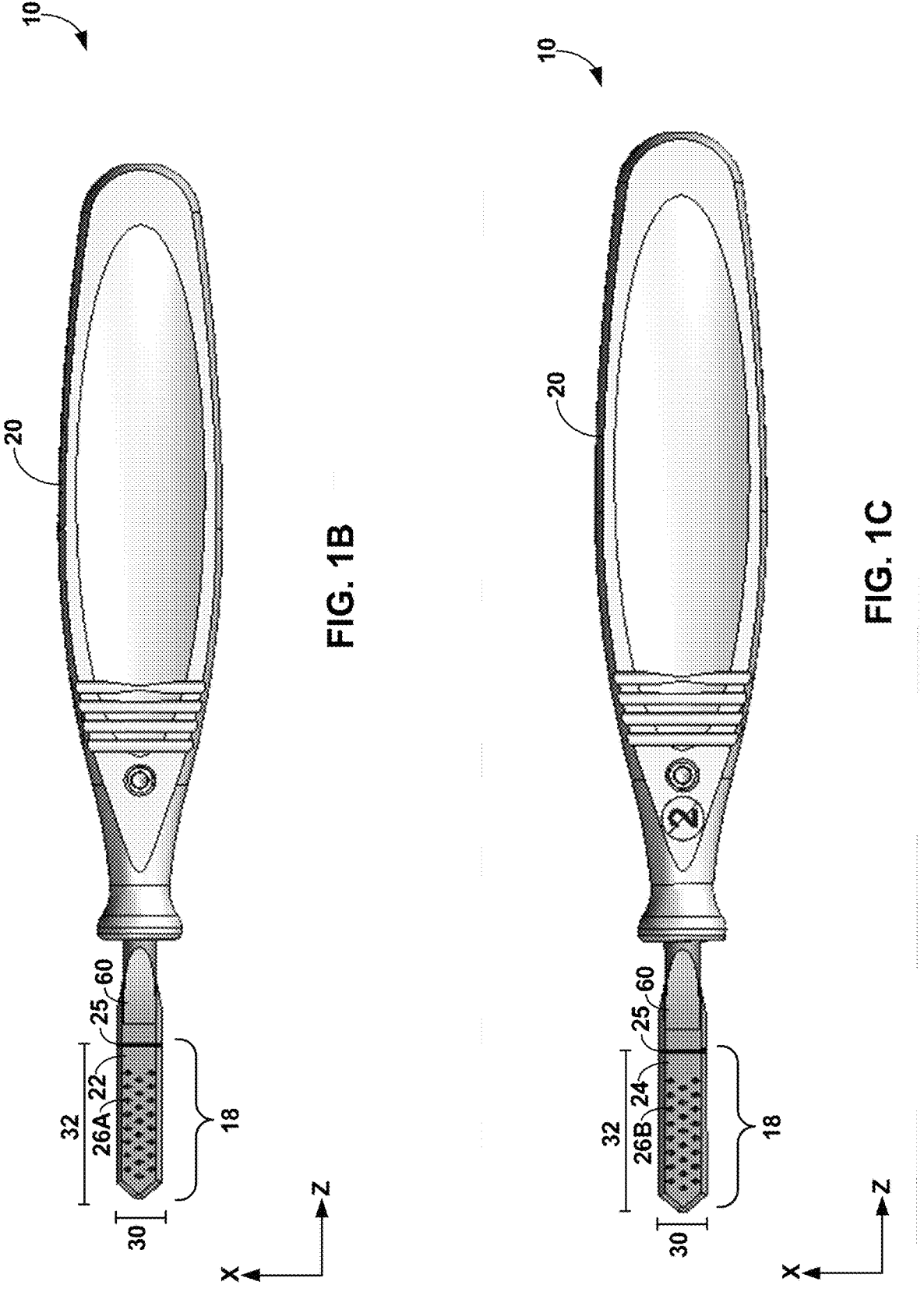

FIGS. 1A-1C (collectively referred to as "FIG. 1") are different views of an example orthopedic rasp 10 according to the disclosure. FIG. 1A is a perspective view of rasp 10, while FIGS. 1B and 1C are top and bottom views, respectively, of rasp 10. As illustrated, rasp 10 includes a body 12 having a length extending from a first end 14 to a second end 16. Body 12 defines a rasp head 18, which may be a region of the body configured and intended to be inserted into the space between a first cuneiform and a second cuneiform within an intercuneiform joint space when using rasp 10. In the illustrated example, rasp 10 includes handle 20 that is operatively connected to the body and is configured to be grasp by a user, allowing the user to manually manipulate the position and force applied by rasp head 18 under hand pressure and control. In various implementations, body 12 and handle 20 may be fabricated as a unitary body (e.g., cut or cast as a single piece of material) or may be fabricated as separate components that are joined together to form a combined structure the does not separate during use.

As will be described in greater detail below, rasp head 18 can be configured to be inserted into an intercuneiform joint space between a first cuneiform and a second cuneiform. Rasp head 18 can include multiple cutting teeth located on one or both sides of the rasp that are effective to prepare the first and/or second cuneiform for fusion. Rasp head 18 can prepare the first and/or second cuneiform for fusion by rasping side surfaces of one or both bones across the intercuneiform joint. For example, rasp head 18 can include multiple cutting teeth located on one or both sides of the rasp head that, upon advancing and retracting the cutting teeth against a side surface of the first cuneiform and/or a second cuneiform (e.g., multiple times through a reciprocating motion) form opposed bleeding bone surface. The multiple cutting teeth carried by rasp head 18 can be used to prepare a lateral side of the first cuneiform and a medial side of the second cuneiform across the intercuneiform joint at locations that contact each other for fusion, when the first cuneiform and the second cuneiform are pressed together to close the intercuneiform joint space. One or more fixation devices can then be applied to the first cuneiform and the second cuneiform across the intercuneiform joint to hold the prepared bone surfaces in contact during bone growth and resulting fusion.

With reference to FIGS. 1B and 1C, body 12 of rasp 10 is illustrated as defining a first widthwise surface 22 and a second widthwise surface 24 in the region of rasp head 18. Second widthwise surface 24 is on an opposite side of body 12 across the thickness of the material defining rasp head 18. First widthwise surface 22 and second widthwise surface 24 may be surfaces of body 12 (e.g., in the X-Z plane indicated on FIGS. 1B and 1C) in the region defining rasp head 18 and that extend perpendicular to the length of the body (in the Z-direction indicated on the figures) and perpendicular to the thickness of the body (in the Y-direction indicated on the figures). In the illustrated configuration, first widthwise surface 22 and second widthwise surface 24 each are flat or planar surfaces within different X-Y planes indicated in FIGS. 1B and 1C (with the two planes being separated by the thickness of rasp head 18). In other implementations, one or both of first widthwise surface 22 and second widthwise surface 24 may be curved, angled, or have other shape characteristics than the configuration specifically illustrated.

Rasp head 18 includes a plurality of cutting teeth 26 extending outwardly from one or both of first widthwise surface 22 and second widthwise surface 24. In some implementations, rasp head 18 includes the plurality of cutting teeth 26 extending outwardly from one only one surface (e.g., first widthwise surface 22) with the opposite surface (e.g., second widthwise surface 24) being devoid of cutting teeth. In these implementations, a clinician may rasp one cuneiform defining an intercuneiform joint using rasp head 18 before flipping the rasp over and rasping the other cuneiform defining the intercuneiform joint using the same side of rasp head 18 used to prepare the first cuneiform. In other implementations, first widthwise surface 22 and second widthwise surface 24 are each configured with a plurality of cutting teeth extending outwardly from a respective on of the widthwise surfaces.

For example, in the illustrated configuration of FIG. 1, first widthwise surface 22 of rasp head 18 includes a first plurality of cutting teeth 26A extending outwardly from the surface, and second widthwise surface 24 includes a second plurality of cutting teeth 26B extending outwardly from the surface. Unless otherwise specified, the first plurality of cutting teeth 26A and the second plurality of cutting teeth 26B will individually and collectively be referred to as the "plurality of cutting teeth 26" for purposes of simplicity in the continued discussion.

As will be described in greater detail, the plurality of cutting teeth 26 may be arranged such that at least some of the plurality of cutting teeth are spaced apart from each other along the length of body 12 (in the Z-direction indicated on the figures). In use, rasp 10 may be inserted into an intercuneiform joint with first end 14 providing or distal or leading end and second end 16 providing a proximal or trailing end. Rasp head 18 may be inserted with the distal end of the rasp entering the joint space before a comparatively proximal portion of the rasp head entering the joint space. Rasp head 18 can be configured with cutting teeth spaced along at least a portion of the length of the rasp head to provide a longitudinally extending array of cutting teeth positioned at different vertical elevations along the length of the rasp.

Each of the plurality of cutting teeth 26 can extend outwardly from a respective widthwise surface of rasp head 18. As a result, each of the plurality of cutting teeth can define a height from an outmost edge of the cutting tooth to a respective widthwise surface of rasp head 18. The size and configuration of the plurality of cutting teeth 26 can vary depending on the amount of bone preparation and aggressiveness of cutting desired to be provided by rasp 10.

Rasp head 18 of rasp 10 may be specifically configured (e.g., sized and/or shaped) to be inserted into an intercuneiform joint between a first cuneiform and a second cuneiform. Rasp head 18 may have a thickness 28 (in the Y-direction indicated on FIG. 1) that is sufficiently small to allow the rasp head to be inserted into the intercuneiform joint while being sufficiently large to avoid undesirable flexing during rasping and/or to allow rasp head 18 to simultaneously contacting rasp both the first and second cuneiforms. In some examples, rasp head 18 has a thickness 28 of at least 0.5 mm, such as at least 0.7 mm, at least 0.8 mm, at least 0.9 mm, at least 1.0 mm, at least 1.1 mm, or at least 1.2 mm. Additionally or alternatively, rasp head 18 may have a thickness 28 less than 2.5 mm, such as less than 2.0 mm, less than 1.8 mm, less than 1.7 mm, less than 1.6 mm, less than 1.5 mm, less than 1.4 mm, less than 1.3 mm, or less than 1.2 mm. For example, rasp head 18 may have a thickness 28 within a range from 0.6 mm to 1.8 mm, such as from 0.7 mm to 1.7 mm, or from 0.8 mm to 1.5 mm.

Thickness 28 may be measured from the outermost edge of the outwardly extending plurality of cutting teeth 26 of one side of rasp head 18 to the owner most edge of the outwardly extending plurality of cutting teeth on the opposite side of the rasp (when configured with cutting teeth on both side surfaces of the rasp). Accordingly, the foregoing example thickness dimensions can include any thickness contribution associated with the height of the plurality teeth. Thickness 28 may be substantially constant over the width and/or length of rasp head 18 or may vary over the width and/or length of the rasp head. When thickness 28 of rasp head 18 varies over the width and/or length of the rasp head, the foregoing example thickness dimensions can represent an average thickness across the rasp head.

Rasp head 18 of rasp 10 can define a width 30 (in the X-direction indicated on FIGS. 1B and 1C) that is sufficiently large to prepare enough bone surface for fusion to achieve a good union between the first cuneiform and the second cuneiform. However, width 30 of rasp head 18 may be comparatively small, e.g., to allow the rasp to be inserted through a comparatively small incision and/or to avoid damaging soft tissue (e.g., tendons, ligaments) adjacent to the intercuneiform joint space when rasping the first cuneiform and the second cuneiform. In some examples, the width 30 of rasp head 18 is at least 2 mm, such as at least 3 mm, at least 4 mm, at least 5 mm, at least 6 mm, or at least 7 mm. Additionally or alternatively, the width 30 of rasp and 18 may be less than 15 mm, such as less than 10 mm, less than 8 mm, less than 7 mm, or less than 6 mm. For example, the width 30 of rasp head 18 may be within a range from 2 mm to 8 mm, such as from 3 mm to 7 mm, from 4 mm to 6 mm, or from 4.5 mm to 5.5 mm.

Width rasp head 18 may be substantially constant over the length of the rasp head or may vary over the length of the rasp head. For example, in the illustrated configuration, both the thickness 28 and width 30 of rasp head 18 are substantially constant over the length of the rasp head. When width 30 of rasp head 18 varies over the length of the rasp head, the foregoing example width dimensions can represent an average width across the rasp head.

Rasp head 18 may define a length 32 (in the Z-direction indicated on FIG. 1) sufficient to allow rasp 10 to be inserted into the intercuneiform joint space between the first cuneiform and the second cuneiform and to allow the rasp to prepare opposed surfaces of the two bones across the joint space. In some examples, rasp head 18 defines a length 32 within a range from 10 mm to 50 mm, such as from 15 mm to 30 mm, from 15 mm to 25 mm, or from 18 mm to 20 mm. In some configurations, rasp head 18 includes a depth marking 25 positioned at a specified distance from first end 14 (e.g., 10 mm, 15 mm, 20 mm, 25 mm, 30 mm). Depth marking 25 can be a visual indicator (e.g., notch, line, size and/or shape transition, marker) to allow the clinician to assess how deep into the intercuneiform joint space rasp 10 has been inserted.

As illustrated in the example of FIG. 1, rasp 10 and/or body 12 can have a length greater than the length 32 defined by the rasp head portion of the structure. Body 12 may or may not have a distinguishing size and/or shape change between the portion of the body defining rasp head 18 in a proximal remainder of the body. Rasp head 18 may be identified as that portion of body 12 configured (e.g., sized and/or shaped) and intended to be inserted into the intercuneiform joint space and to provide a working surface or surfaces for rasping the first cuneiform and the second cuneiform. In the illustrated configuration, for instance, rasp head 18 extends from first end 14 to depth marking 25. In some configurations, rasp 10 defines an overall length (e.g., from the first end 14 to the second end 16) within a range from 50 mm to 200 mm, such as from 100 mm to 150 mm.

Figure 2A:
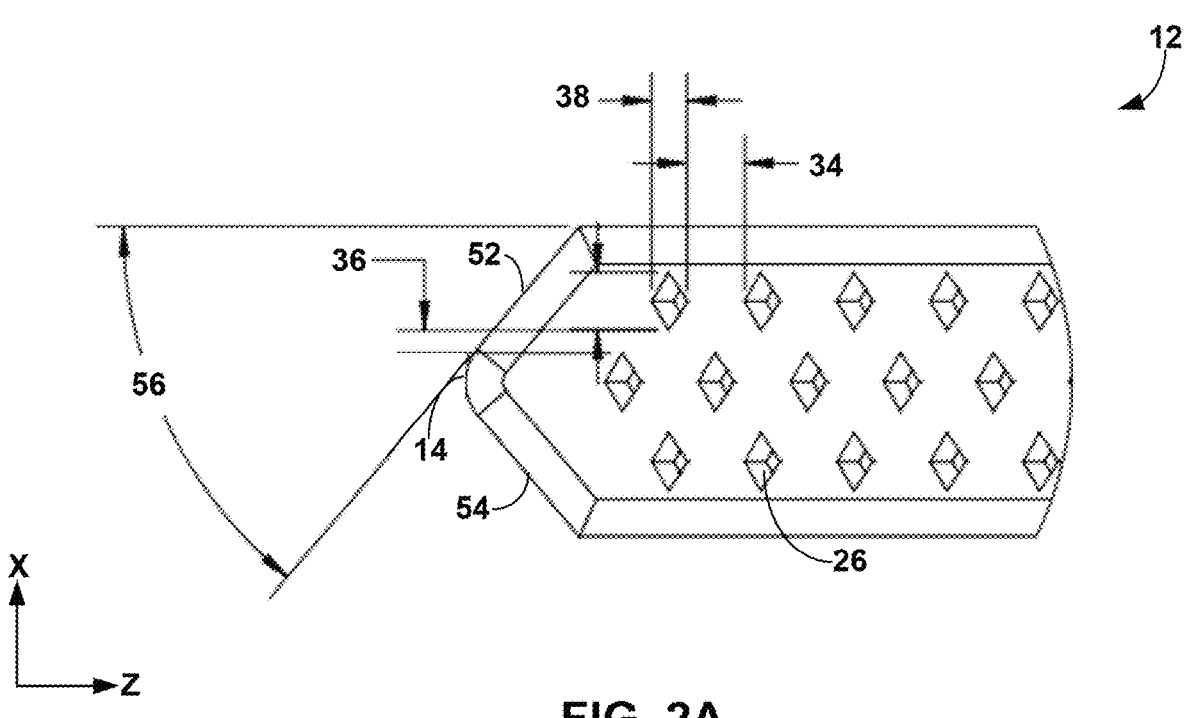
FIGS. 2A and 2B are an enlarged top view and side sectional view, respectively, of a first end region of the example rasp from FIG. 1.
Figure 2B:
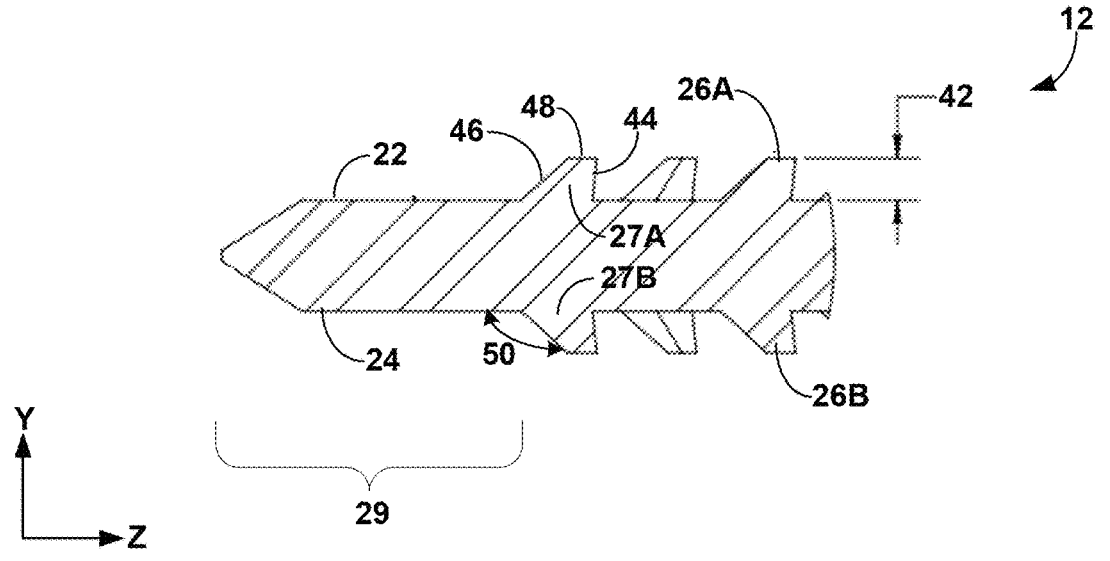

FIGS. 2A and 2B (collectively referred to as "FIG. 2") are an enlarged top view and side sectional view, respectively, of a first end region of rasp 10, encompassing rasp head 18, from FIG. 1 illustrating an example leading end configuration of the rasp and an example cutting tooth configuration of the rasp. As shown in the example of FIG. 2, rasp head 18 includes a plurality of cutting teeth 26 extending outwardly (e.g., in the direction of the thickness of the rasp) from one or both widthwise surfaces of the rasp. In particular, in the illustrated example, of rasp head 18 includes a first plurality of cutting teeth 26A extending outwardly from first widthwise surface 22 of rasp head 18 and a second plurality of cutting teeth 26B extending outwardly from second widthwise surface 24.

Rasp 10 can utilize a variety of different cutting teeth configuration. In some implementations, each cutting tooth 26 extends across substantially the entire width of rasp head 18, with different cutting teeth separated from each other along the length of the cutting. In other implementations, including that illustrated in FIG. 2, the plurality of cutting teeth 26 are spaced apart from each other both lengthwise and widthwise across rasp head 18. As a result, rasp head 18 can include at least some cutting teeth 26 spaced apart from each other along the length of body 12 (in the Z-direction indicated) and/or at least some cutting teeth 26 spaced apart from each other along the width of body 12 (in the X-direction indicated).

The relative spacing between individual cutting teeth 26 can vary, e.g., based on the size and configuration of the cutting teeth and desired aggressiveness of cutting provided by the cutting teeth. Further, the size of each cutting tooth 26 can vary, e.g., based on the desired aggressiveness of cutting provided by the cutting teeth. FIG. 2A illustrates the plurality of cutting teeth 26 being spaced apart from each other along the length of body 12 (in the Z-direction indicated) to provide a lengthwise spacing 34 between adjacent pairs of the plurality of cutting teeth. Lengthwise spacing 34 may be measured from a proximal or back end of a distal tooth to a distal or front end of an immediately-adjacent proximal tooth. In some examples, the lengthwise spacing 34 between adjacent pairs of the cutting teeth 26 is within a range from 0.25 mm to 2 mm, such as 0.5 mm to 1.5 mm, or from 0.9 mm to 1.2 mm. The lengthwise spacing 34 may be the same between each adjacent pair of cutting teeth or may vary (e.g., such that some cutting teeth are spaced farther from adjacent cutting teeth than the spacing exhibited by other pairs of cutting teeth).

When the plurality of cutting teeth 26 are spaced apart from each other along the width of body 12 (in the X-direction indicated), a widthwise spacing 36 can be provided between adjacent pairs of the plurality of cutting teeth. In some examples, the widthwise spacing 36 between adjacent pairs of the cutting teeth 26 is within a range from 0.1 mm to 1.0 mm, such as from 0.3 to 0.7 mm, or from 0.4 mm to 0.6 mm. The widthwise spacing 36 may be the same between each adjacent pair of cutting teeth or may vary (e.g., such that some cutting teeth are spaced farther from adjacent cutting teeth than the spacing exhibited by other pairs of cutting teeth). Further, when some or all of the plurality of cutting teeth 26 are spaced apart from adjacent cutting teeth along the width of body 12, the cutting teeth may be symmetrically arrayed (e.g., into ordered and/or repeating patterns) or asymmetrically arrayed across a widthwise surface of the rasp. For example, the plurality of cutting teeth 26 may be arranged in one or more longitudinally-extending columns which, in the illustrated arrangement, is shown as three longitudinally-extending columns.

While each of the plurality of cutting teeth 26 may have a variety of different sizes, in some examples, each cutting tooth has a length 38 (in a direction parallel to the length of rasp 10) within a range from 0.25 mm to 1.0 mm, such as from 0.5 mm to 0.85 mm, or from 0.65 mm to 0.75 mm. Each cutting tooth may have a width 40 (in a direction parallel to the width of rasp 10) within a range from 0.5 mm to 1.5 mm, such as from 0.8 mm to 1.3 mm, or from 1.0 mm to 1.2 mm. In some examples, the width 40 of each cutting tooth 26 is larger than the length 38 of the cutting tooth.

With reference to FIG. 2B, each cutting tooth can extend outwardly from a widthwise surface of body 12. For example, as illustrated, the first plurality of cutting teeth 26A can extend outwardly a first direction from a first widthwise surface 22, and the second plurality of cutting teeth 26B can extend outwardly a second direction (e.g. opposite the first direction) from a second widthwise surface 24. Each of the plurality of cutting teeth 26 may outwardly from a respective widthwise surface a distance 42, within may be within a range from 0.25 mm to 0.55 mm, such as from 0.3 to 0.45 mm, or from 0.35 to 0.40 mm.

The plurality of cutting teeth 26 may be configured for bidirectional cutting or unidirectional cutting. When configured for bidirectional cutting, each cutting tooth may have a cutting surface on both a proximal and distal side of the cutting tooth. As a result, when rasp 10 is moved (e.g., reciprocated up and down) the cutting teeth on the rasp may cut in both movement directions. When configured for unidirectional cutting, each cutting tooth may have a cutting surface on one side of the cutting tooth (e.g., a proximal or distal side of the cutting tooth) but be devoid of a cutting surface on the opposite side of the cutting tooth. When so configured, the cutting teeth on the rasp may cut in one movement direction (e.g., as rasp 10 is moved upwardly or downwardly) but not be configured to cut in the opposite movement direction.

In the illustrated arrangement, the plurality of cutting teeth 26 are shown as being configured as unidirectional cutting teeth in which there is a single cutting surface 44 positioned on a proximal or trailing side of the cutting tooth. For example, each cutting tooth may be defined by a tapered leading surface 46 that extends outwardly at an angle from a respective widthwise surface. Tapered leading surface 46 may be tapered in a direction towards the proximal for second end 16 of rasp 10. Trailing cutting surface 44 extends outwardly from a respective widthwise surface and can join tapered leading surface 46 and an outer side of the cutting tooth. For example, trailing cutting surface 44 can intersect tapered leading surface 46 at an apex or, as illustrated, an outer side edge 48 extending between trailing cutting surface 44 and tapered leading surface 46.

Configuring cutting tooth 26 with a tapered leading surface 46 may be useful to help provide a tapered surface that eases insertion of rasp 10 into the intercuneiform joint space. Tapered leading surface 46 may taper at an angle 50 measured relative to the widthwise surface from which the tapered leading surface extends. In some examples, tapered leading surface 46 tapers at an angle 50 within a range from 115° to 130°, such as from 120° to 125°. Trailing cutting surface 44 may extend perpendicularly outwardly relative to the widthwise surface from which the cutting surface extends, or may extend at an angle (e.g., directed proximally).

The end of body 12 may or may not be tapered to help facilitate insertion of rasp 10 into the intercuneiform joint space (e.g., helping to pry the first cuneiform and the second cuneiform away from each other as the instrument is inserted into the joint). In some examples, such as the example illustrated in FIG. 2A, the distal end of body 12 may be tapered across the width of the body, narrowing the cross-sectional width of the body at the distalmost end as compared to a region offset from the distalmost end. For example, body 12 may define a first leading surface 52 extending angularly outwardly from the first end 14 of the body and a second leading surface 54 extending angularly outwardly from the first end 14 of the body in an opposite direction from the first leading surface. The first leading surface 52 and the second leading surface 54 can converge at or adjacent the first end 14 of body 12 in flare outwardly in a direction toward the proximal or second end 16 of the body. In some configurations, the first leading surface 52 and/or the second leading surface 54 extends angularly outwardly from the first end 14 of the body at an angle 56 measured relative to a longitudinal axis at the outer end of each respective leading surface. In some examples, angle 56 is within a range from 30° to 70°, such as from 40° to 60°, or from 45° to 55°.

In addition to or in lieu of tapering body 12 across the width of the body at the first end 14, the thickness of the body may be tapered at distal end 14 (e.g., to aid insertion of rasp 10 into the joint space. For example, with reference to FIG. 2B, the thickness of body 12 at distal end 14 may be taped (in the Y-direction indicated on the figure). Body 12 may be tapered at first end 14 in a first direction across the thickness of the body (e.g., from first end 14 toward first widthwise surface 22) and in a second direction across the thickness of the body (e.g., from first end 14 toward second widthwise surface 24). The two taper planes may intersect each other at a location that is substantially centered across the thickness of the body. This configuration may be referred to as a dual-sided taper configuration. In other configurations, body 12 may not be tapered across the thickness or may only be tapered from one side. While the angle of taper can vary, in some configurations, one or both sides body 12 taper at first end 14 at an angle within a range from 15 degrees to 75 degrees, such from 20 degrees to 50 degrees, from 25 degrees to 45 degrees, or from 30 degrees to 35 degrees. Tapering or chamfering the tip of rasp 10 can be helpful to provide a wedge shape that can help pry open the intercuneiform joint space during insertion of the instrument.

The plurality of cutting teeth 26 can be arrayed to extend from first end 14 of body 12 proximally along the length of rasp head 18. In some configurations, rasp head 18 includes a region devoid of cutting teeth (on first widthwise surface 22 and/or second widthwise surface 24) between the first end 14 of the body and a first or distal-most cutting tooth. For example, with reference to FIG. 2B, rasp head 18 includes a distal-most cutting tooth 27, which is illustrated as a distal-most cutting tooth 27A on first widthwise surface 22 and a co-linearly positioned distal-most cutting tooth 27B on second widthwise surface 24. Rasp head 18 defines a region 29 devoid of cutting teeth between the first end 14 of body 12 and the distal-most cutting tooth 27. First widthwise surface 22 and/or second widthwise surface 24 may be smooth (e.g., planar) surfaces over region 29. Configuring rasp 10 with a leading region 29 devoid of cutting teeth may be helpful to enable easier insertion of the rasp into the intercuneiform joint. When configured with region 29, the region may have a length from the first end 14 of body 12 and the distal edge of distal-most cutting tooth 27 within a range from 2 mm to 6 mm, such as from 3 mm to 5 mm, or from 4 mm to 5 mm, such as approximately 4.5 mm (plus or minus 5%).

With further reference to FIG. 1, body 12 of rasp 10 can include a shank 60 extending from rasp head 18. Shank 60 may be integrally formed with or operatively coupled to rasp head 18. Shank 60 may be in extending part of body 12 from the working portion of the rasp. In some examples, shank 60 may define a handle or be connected to handle 20.

In general, rasp 10, including body 12 and handle 20, can be formed of any desired material or combinations of materials. Typically, body 12 (including rasp head 18) will be fabricated of metal to form a sharp cutting surface, such as steel (e.g., stainless steel), titanium, or the like, although may be formed of ceramic or other sharpenable materials. Handle 20 may be formed of a variety of materials, including one or more metals and/or polymeric materials.

Figure 3:
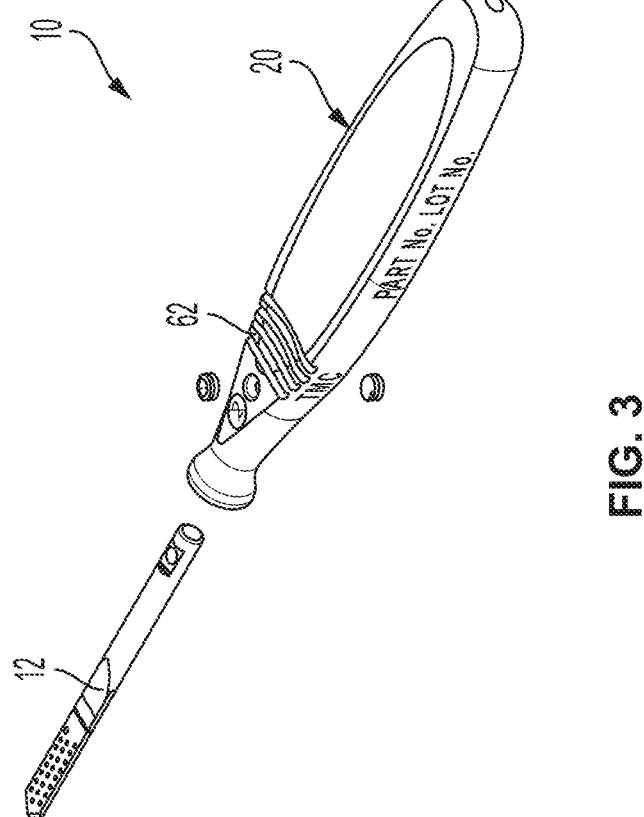
FIG. 3 is exploded perspective view of the example rasp from FIG. 1.

FIG. 3 is exploded perspective view of rasp 10 illustrating an example body and handle configuration. In some configurations, body 12 and handle 20 are formed as a unitary structure (e.g., via casting, milling) defined by a single type of material. In other configurations, body 12 and handle 20 may be formed as separate structures joined together to couple the cutting head to the handle for subsequent use. In some such configurations, handle 20 may be formed of a different material (e.g., a polymeric material) then body 12 (which may be formed of metal material), e.g., for increased grip ability and/or comfort and holding. For example, handle 20 may define a receiving cavity, and an end of body 12 opposite leading end 14 can be inserted into the receiving cavity to interconnect the handling cutting head. Fixation means (e.g., adhesive, screws such as set screws, bolts, welding) may be used to permanently affix the cutting head to the handle. In other configurations, body 12 may be detachably attached to handle 20 to allow the handle to be used with different interchangeable cutting heads (e.g., each having the same configuration or having different configurations from each other).

Handle 20 may generally be configured to be gripped manually by the hand of a clinician using rasp 10. Handle 20 may have an enlarged cross-sectional size (e.g., width, thickness) relative to body 12 to provide a larger surface for grasping. In some configurations, handle 20 includes surface texturing 62, such as knobs, ribs, knurls, and/or other features that facilitate gripping of the handle without slippage. While handle 20 may generally be designed to be gripped manually by the hand of the clinician, in other configurations, body 12 and/or handle 20 may be designed to be inserted into a powered hand instrument that can drive movement of rasp 10.

In the illustrated arrangements, handle 20 is illustrated as extending co-linearly with rasp head 18 of body 12. That is, the longitudinal axis defined by handle 20 is illustrated as extending co-linearly with a longitudinal axis extending through rasp head 18. In other configurations, handle 20 (the entire handle or portion thereof) may be offset from and/or angled relative to the longitudinal axis extending through rasp head 18.

As briefly discussed above, rasp instrument 10 can be used during a variety of different procedures, including as part of a bone alignment procedure. Rasp 10 can be used to prepare opposed surfaces of a first cuneiform and a second cuneiform across an inner cuneiform joint for fixation and fusion. In some examples, the preparation of the intercuneiform joint using rasp 10 for fusion is performed in conjunction with a procedure in which one or more bones of the foot are realigned. To further understand example techniques according to the disclosure, the anatomy of the foot will be described with respect to FIGS. 4A and 4B.

Figure 4B:
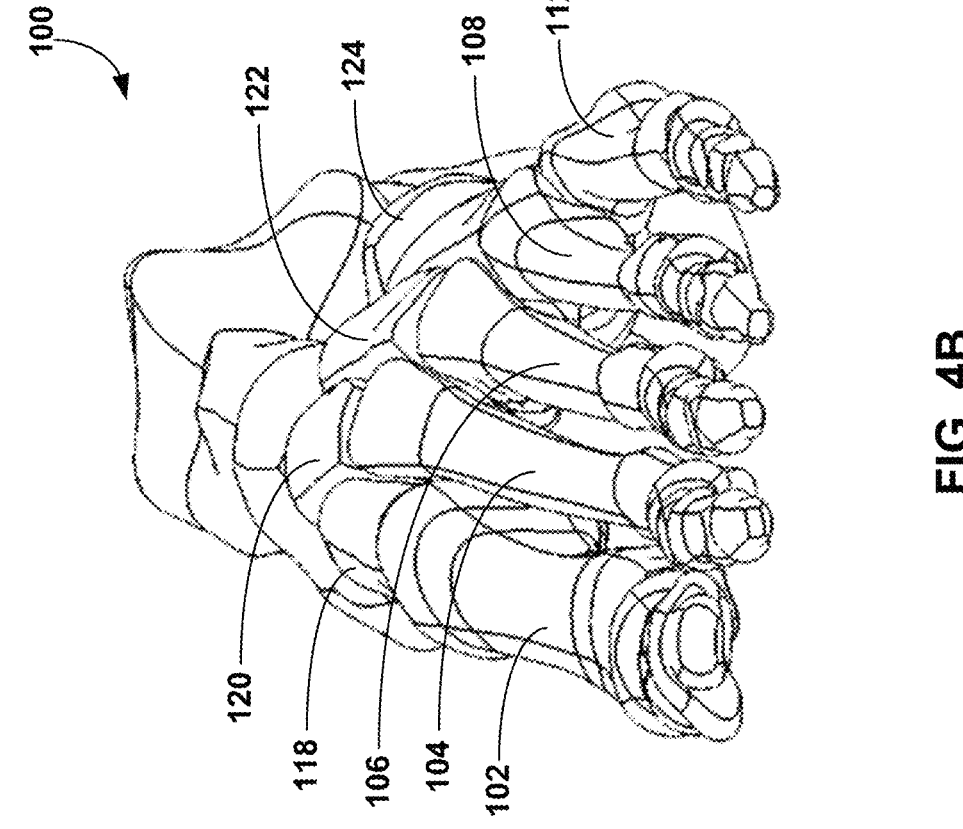
FIGS. 4A and 4B are top and front views, respectively, of a foot showing normal metatarsal alignment positions.
Figure 4A:
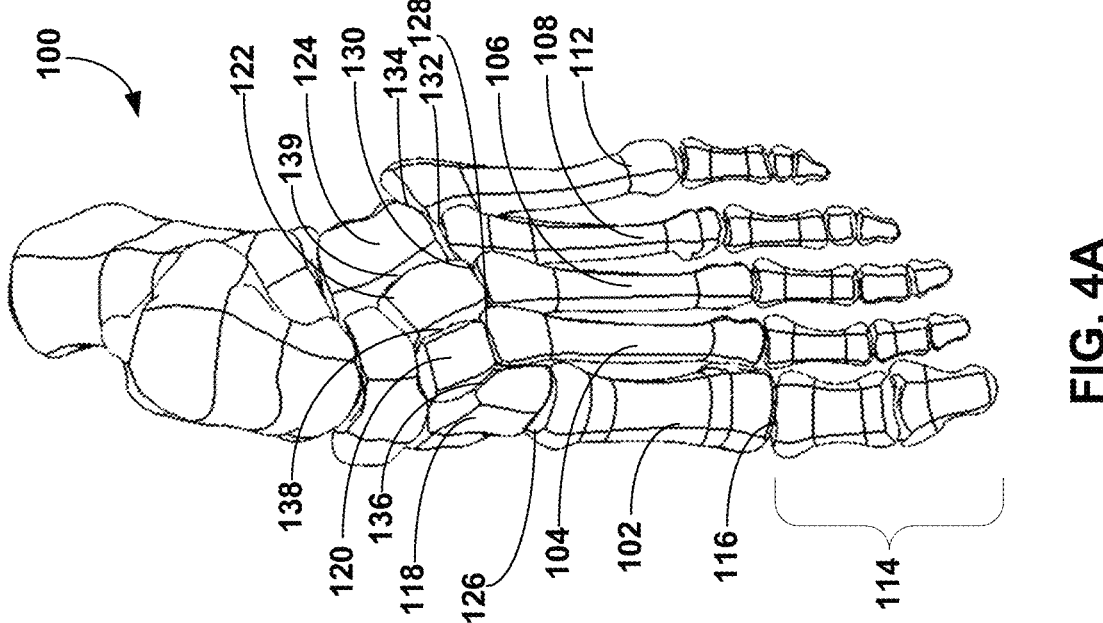

FIGS. 4A and 4B are top and front views, respectively, of a foot 100 showing normal metatarsal alignment positions. Foot 100 is composed of multiple bones including a first metatarsal 102, a second metatarsal 104, a third metatarsal 106, a fourth metatarsal 108, and a fifth metatarsal 112. First metatarsal 102 is on a medial-most side of the foot while fifth metatarsal 112 is on a lateral-most side of the foot. The metatarsals are connected distally to phalanges 114 and, more particularly, each to a respective proximal phalanx. The joint 116 between a metatarsal and a corresponding opposed proximal phalanx is referred to as a metatarsophalangeal ("MTP") joint. The first MTP joint is labeled as joint 116 in FIG. 4A, although second, third, fourth, and fifth MTP joints are also illustrated in series adjacent to the first MTP joint.

The first metatarsal 102 is connected proximally to a medial cuneiform 118, while the second metatarsal 104 is connected proximally to an intermediate cuneiform 120, and the third metatarsal 106 is connected proximally to lateral cuneiform 122. The fourth and fifth metatarsals 108, 112 are connected proximally to the cuboid bone 124. The joint between a metatarsal and opposed bone (cuneiform, cuboid) is referred to as the tarsometatarsal ("TMT") joint. FIG. 4A designates a first TMT joint 126, a second TMT joint 128, a third TMT joint 130, a fourth TMT joint 132, and a fifth TMT joint 134. The angle between adjacent metatarsals is referred to as the intermetatarsal angle ("IMA").

The joint between one cuneiform and an adjacent cuneiform is an intercuneiform joint. FIG. 4A designates a first intercuneiform joint 136 between medial cuneiform 118 and intermediate cuneiform 120 and a second intercuneiform joint 138 between intermediate cuneiform 120 and lateral cuneiform 122. FIG. 4A also illustrates a cuneiform-cuboid joint 139 between lateral cuneiform 122 and a cuboid 124.

In the example of FIGS. 4A and 4B, foot 100 is illustrates as having generally normally aligned metatarsals. Normal metatarsal alignment may be characterized, among other attributes, by a low intermetatarsal angle (e.g., 9 degrees or less, such as 5 degrees or less) between the first metatarsal and the second metatarsal. In addition, the lesser metatarsals may be generally parallel to a longitudinal axis bisecting the foot proximally to distally.

Figure 5:
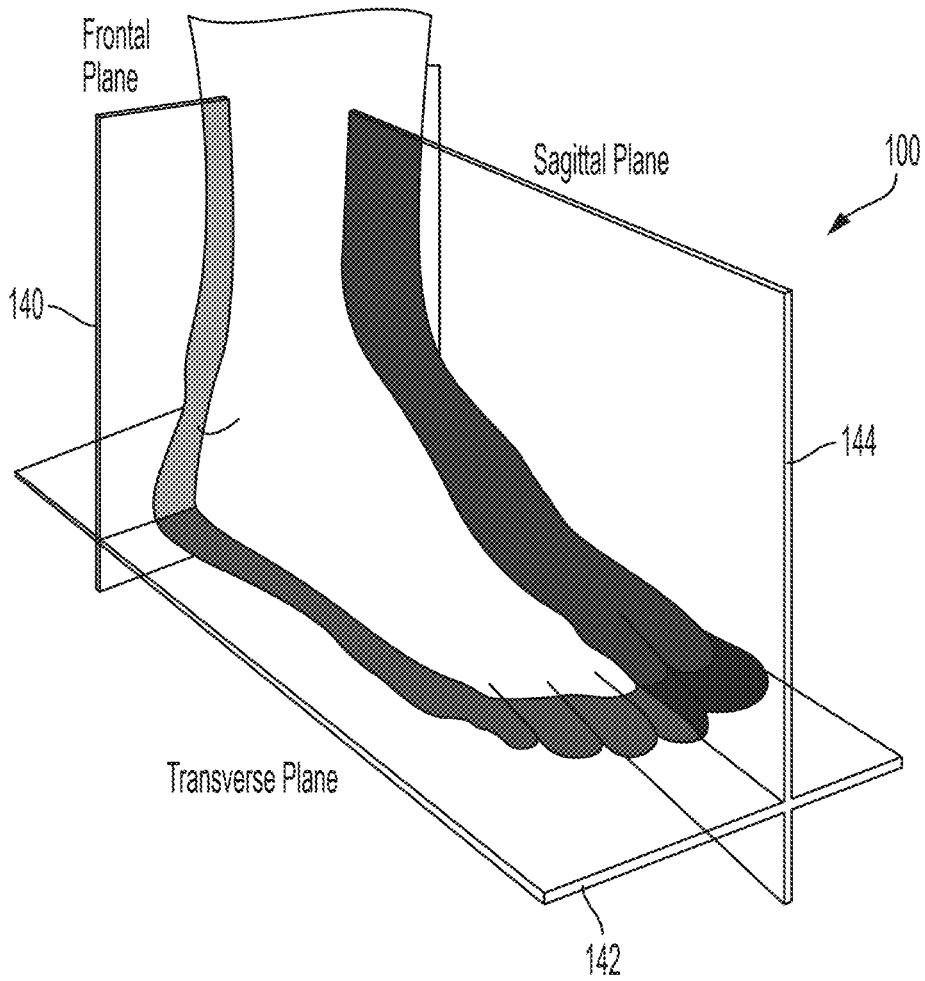
FIG. 5 illustrates the different anatomical planes of a foot.

FIG. 5 illustrates the different anatomical planes of foot 100, including frontal plane 140, transverse plane 142, and sagittal plane 144. The frontal plane 140, which is also known as the coronal plane, is generally considered any vertical plane that divides the body into anterior and posterior sections. On foot 100, the frontal plane 140 is a plane that extends vertically and is perpendicular to an axis extending proximally to distally along the length of the foot. The transverse plane 142, which is also known as the horizontal plane, axial plane, or transaxial plane, is considered any plane that divides the body into superior and inferior parts. On foot 100, the transverse plane 142 is a plane that extends horizontally and is perpendicular to an axis extending dorsally to plantarly (top to bottom) across the foot. Further, the sagittal plane 144 is a plane parallel to the sagittal suture which divides the body into right and left halves. On foot 100, the sagittal plane 144 is a plane that extends vertically and intersects an axis extending proximally to distally along the length of the foot. For patients afflicted with certain bone misalignments, one or more of metatarsals may be deviated medially in the transverse plane (e.g., in addition to or in lieu of being rotated in the frontal plane and/or being deviated in the sagittal plane relative to clinically defined normal anatomical alignment for a standard patient population).

Figure 6:
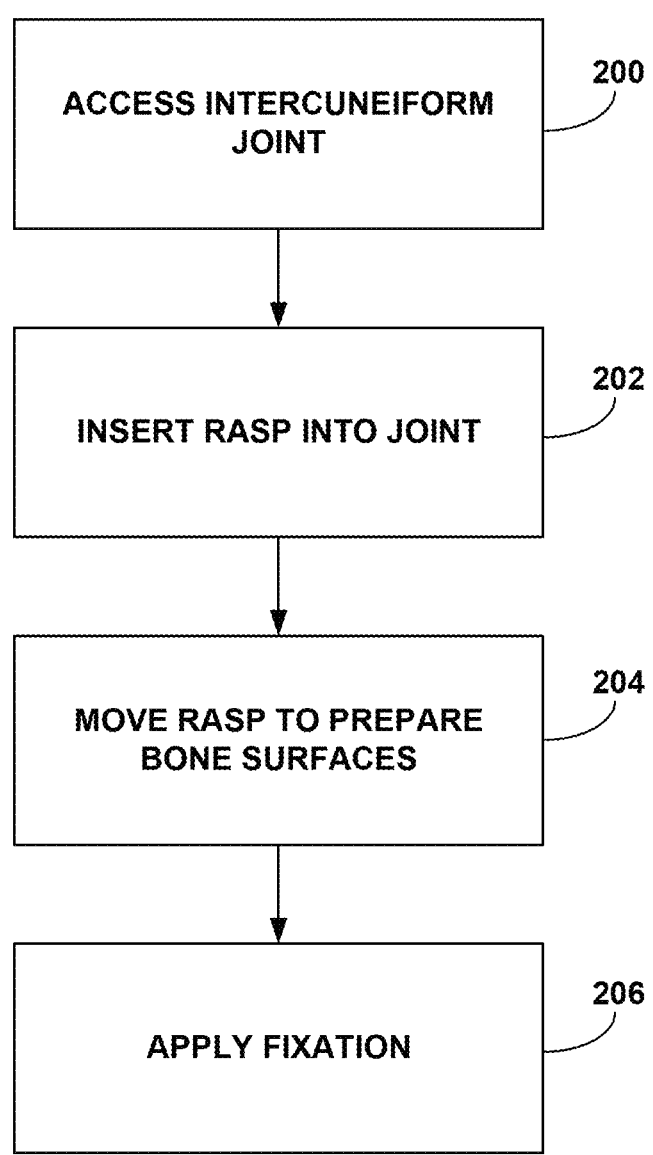
FIG. 6 is a flow diagram of an example technique for preparing an intercuneiform joint for fusion that can be performed utilizing a rasp according to disclosure.
Figure 7:
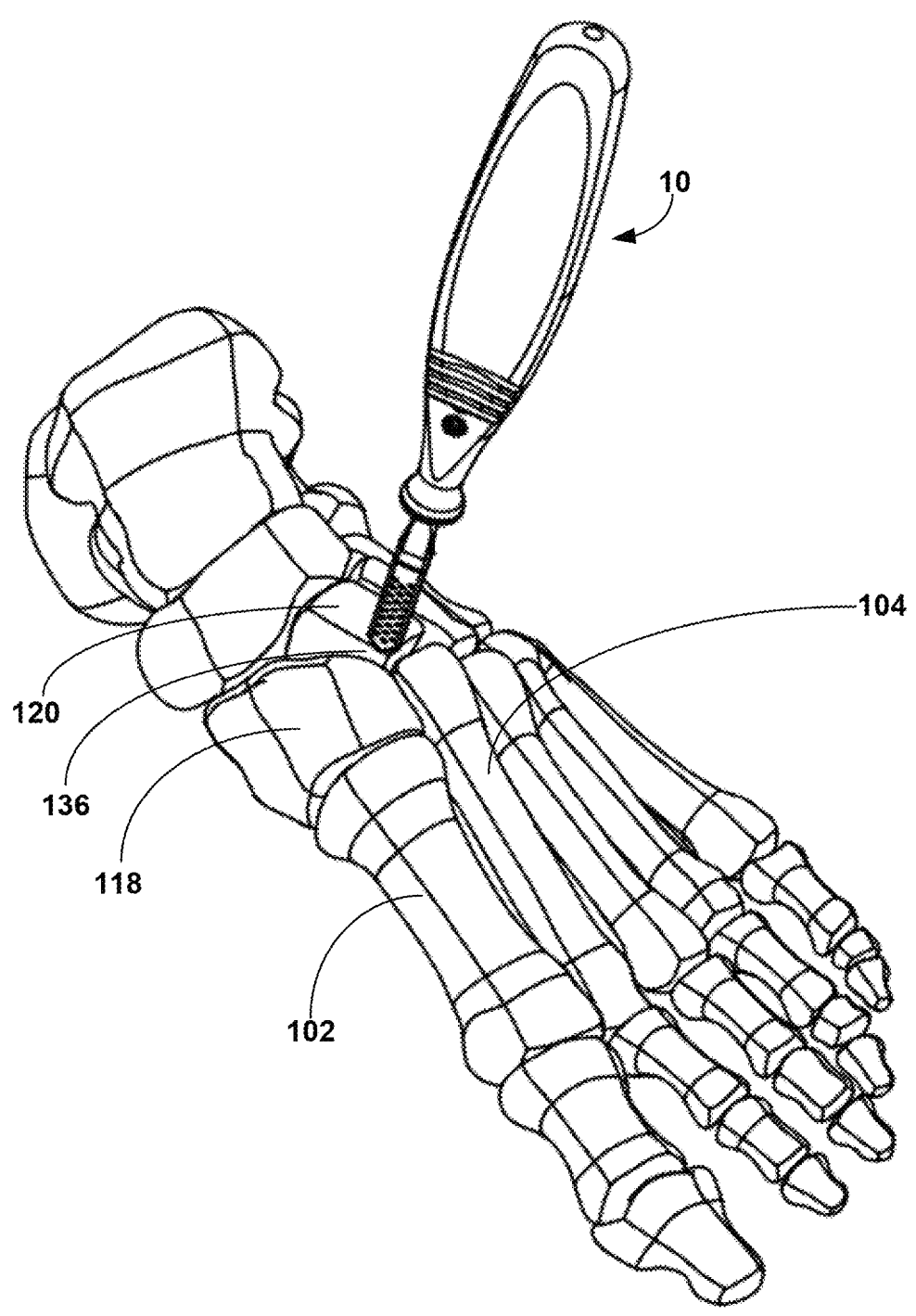
FIGS. 7-9 are perspective illustrations of example steps that can be performed during an intercuneiform joint preparation using a rasp.
Figure 8:
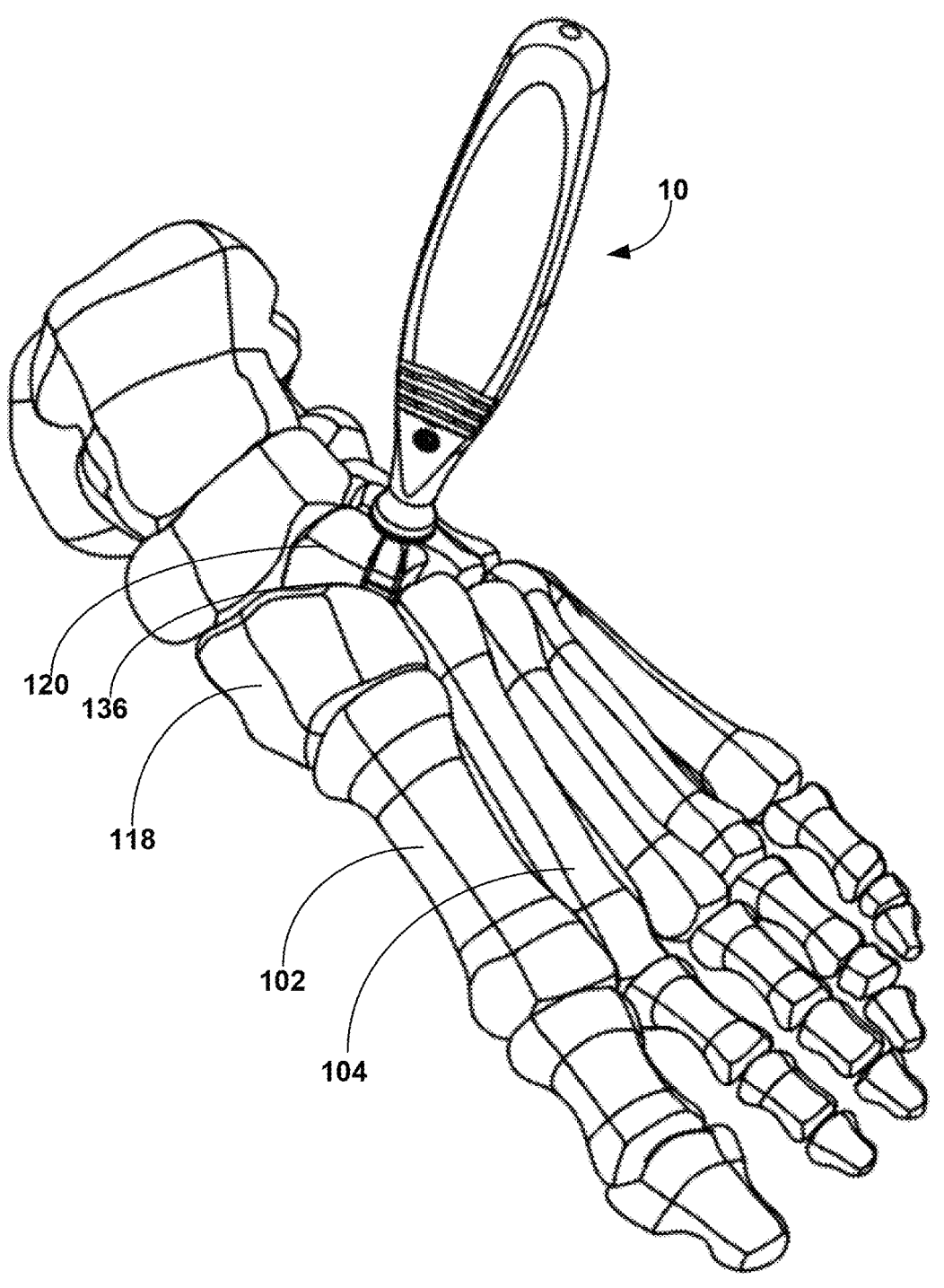

FIG. 6 is a flow diagram of an example technique for preparing an intercuneiform joint for fusion that can be performed utilizing a rasp instrument 10 according to disclosure. The example technique will be described in conjunction with a bone realignment procedure in which a metatarsal is moved in a TMT joint prepared for fusion. An intercuneiform joint preparation technique can be performed for a variety of additional or different applications other than the specific example described with respect FIG. 6. The example technique of FIG. 6 with be described with respect to example procedure steps illustrated in FIGS. 7-9.

The example technique of FIG. 6 involves surgically accessing the intercuneiform joint (200). The clinician can make an incision through the skin of the patient on the dorsal side of the foot over the intercuneiform joint being accessed, such first intercuneiform joint 136 between medial cuneiform 118 and intermediate cuneiform 120 (or other joints defined by other bone pairs as defined herein). In some examples, the clinician makes a comparatively small, minimally invasive incision to access the intercuneiform joint, such as an incision less than 50 mm, less than 35 mm, less than 25 mm, less than 20 mm, or less than 15 mm. The incision may extend from a distal end of intercuneiform joint proximally along a length of the joint or adjacent thereto.

With the intercuneiform joint exposed, the clinician can insert rasp 10 into the intercuneiform joint in the technique of FIG. 6 (202). For example, with reference to FIGS. 7 and 8, the clinician can insert orthopedic rasp 10 into the first intercuneiform joint 136 between medial cuneiform 118 and intermediate cuneiform 120. The clinician may insert at least a portion of rasp head 18 of rasp 10 into the joint. Depending on the orientation of the incision and joint, the clinician may insert the distal end of rasp 10 plantarly (downwardly) into intercuneiform joint 136. In some examples, rasp 10 includes a depth marking 25, and the clinician inserts the rasp down into the joint to a depth indicated by the depth marking (or a lesser position below the depth marking). Rasp 10 may include a handle 20 manually graspable by the clinician such that, when the clinician inserts rasp 10 into intercuneiform joint 136, the insertion is controlled via and movement of the clinician.

While the clinician can insert rasp 10 at a variety of locations (in the distal to proximal direction) along the intercuneiform joint, in some applications, the clinician inserts the rasp at or adjacent to a distal end of the joint. For example, the clinician may insert rasp 10 into intercuneiform joint 136 along a distalmost half of the joint, such as a distalmost quarter of the joint, or a distalmost for the joint. In other applications, the clinician may additionally or alternatively insert the rasp in a proximal portion of the joint.

With rasp 10 partially or fully inserted into the intercuneiform joint, the technique of FIG. 6 includes moving the rasp relative to one or both bones forming the joint (204). For example, the clinician can move the plurality of cutting teeth 26 against and relative to medial cuneiform 118 and intermediate cuneiform 120. As the cutting teeth move against a respective one of the bones, the cutting teeth may cut partially into or fully through a cortex of the bone. This can create a bleeding bone surface that can facilitate fusion with an opposed bleeding bone surface.

In some implementations, such as when rasp 10 is configured with cutting teeth 26 only on a single side of the rasp, the clinician can move rasp against and relative to one of medial cuneiform 118 and intermediate cuneiform 120, preparing a surface of the bone, and then flip the rasp over and move the rasp against and relative to the other bone, preparing a surface of the other bone. In implementations when rasp 10 is configured with a first plurality of cutting teeth 26A in a second plurality of cutting teeth 26B on opposed faces of the rasp, the clinician may use one set of cutting teeth pair a surface of one bone and the other set of cutting teeth to repair an opposite surface on the other bone.

For example, the clinician can move the first plurality of cutting teeth 26A carried by the first side of the rasp relative to an against the lateral side of medial cuneiform 118 and move the second plurality of cutting teeth 26B carried by the second side of the rasp relative to an against the medial side of intermediate cuneiform 120 without flipping the rasp. In some examples, the clinician can move rasp 10 to simultaneously prepare the lateral surface of medial cuneiform 118 and the medial surface of intermediate cuneiform 120. For example, the intercuneiform joint may be sufficiently small compared to the thickness of rasp head 18 such that, when the rasp is moved relative to the joint, the cutting teeth of the opposed faces of the rasp simultaneously contact and move against the respective bones defining the joint.

The clinician may move rasp 10 dorsally and plantarly (up and down) within the intercuneiform joint one or more times to prepare the opposed surfaces of the bones defining the joint. For example, the clinician may move rasp 10 dorsally and plantarly a plurality of times in a reciprocating (e.g., repeating) pattern of movement. Each pass of the rasp against the surface of a bone may remove an additional amount of the bone (and/or cartilage in/or tissue surrounding the bone) to prepare the bone for fusion. As the clinician moves rasp 10 within the intercuneiform joint dorsally and plantarly, the clinician may or may not entirely remove the rasp from the joint before reinserting the rasp into the joint during a particular pass. When rasp 10 is configured with unidirectional cutting teeth, the rasp may cut bone when moving in a particular direction (e.g., dorsally out of the intercuneiform joint) without substantially cutting bone when moving in the opposite direction (e.g., plantarly into the intercuneiform joint).

The amount of surface area prepared on each cuneiform by rasp 10 may vary, e.g., based on the size of the rasp in the movement pattern of the rasp. In some applications, the clinician translates rasp 10 substantially orthogonally to the joint (e.g., dorsally and plantarly) without substantially translating the rasp distally to proximally in the joint. As a result, the surface of the cuneiforms prepared by the rasp may be confined to the location in the dorsal to proximal direction of the intercuneiform joint to where the rasp was placed in the joint. The prepared surface of each cuneiform may have a width corresponding to the width of the rasp (e.g., the same or substantially the same as the width of the rasp).

Figure 9B:
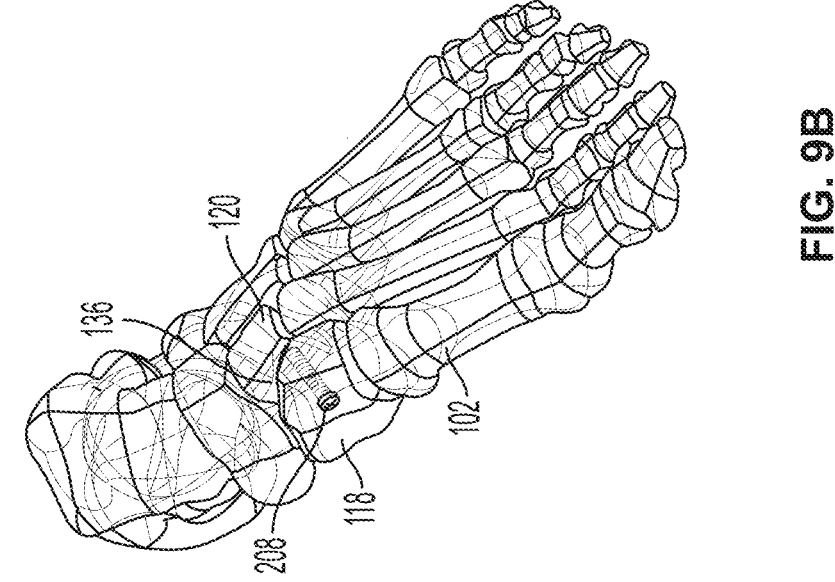
Figure 9A:
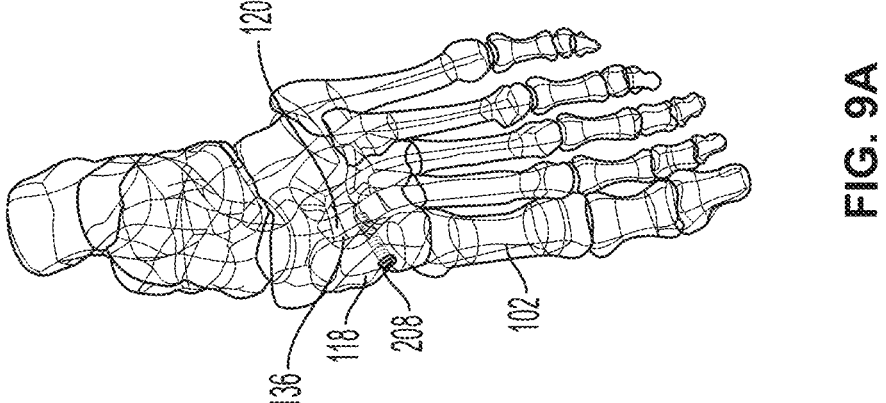

With the intercuneiform joint prepared using rasp 10, the example technique of FIG. 6 includes applying a fixation device across the joint to hold the prepared cuneiforms for fusion (206). For example, FIGS. 9A and 9B (collectively "FIG. 9") are a top view and a perspective view, respectively, of a foot showing an example fixation device applied across a prepared intercuneiform joint. With reference to FIG. 9, the clinician can apply an example fixation device 208 to medial cuneiform 118 into intermediate cuneiform 120 across intercuneiform joint 136. The fixation device may stably hold the prepared surface of medial cuneiform 118 relative to (e.g., against and/or in contact with) the opposed prepared surface of intermediate cuneiform 120 for fusion, allowing bone growth in union across the joint through natural healing occurring following preparation and fixation of the joint.

A variety of different fixation devices 208 can be used to fixate the cuneiforms together across the joint. Example fixation devices that can be used as fixation device 208 include one or more of a plate, a screw, a staple, and/or a pin. In some examples, the fixation device is applied across the intercuneiform joint by extending externally over the joint. For example, the fixation device may be a plate or staple that is secured on one side to one cuneiform in the opposite side to another cuneiform, with the plate or staple bridging across the intercuneiform joint.

Additionally or alternatively, the fixation device may be positioned internally through the intercuneiform joint (e.g., an intramedullary fixation device). For example, the fixation device may be inserted through the intercuneiform joint space. In some examples, the fixation device is implemented using one or more screws that are inserted through the intercuneiform joint space. For example, the one or more screws may be inserted through the medial cuneiform 118 (e.g., from a medial side of the medial cuneiform) and into the intermediate cuneiform 120 (e.g., extending in a lateral direction) crossing intercuneiform joint 136. The clinician may or may not apply a compressive force across the intercuneiform joint to press the prepared surfaces of the cuneiforms together prior to or while attaching one or more fixation devices.

As discussed above, preparation and fixation of an intercuneiform joint may be performed in conjunction with a metatarsal realignment procedure. For example, preparation and fixation of one or more intercuneiform joints using a rasp may be performed in conjunction with realignment of first metatarsal 102 and/or one or more lesser metatarsals, such as second metatarsal 104 and/or and third metatarsal 106. Preparation and fixation of one or more intercuneiform joints using a rasp may be performed before, after, or at least partially concurrent with the process of realigning, preparing, and/or fixating one or more metatarsals as part of a metatarsal realignment procedure.

For example, the clinician may move one or more metatarsals to a moved position, prepare the end faces of the bones forming the tarsometatarsal joint of the metatarsal being moved (e.g., before and/or after moving the metatarsal), and apply one or more metatarsal fixation devices across the prepared tarsometatarsal joint. The clinician may thereafter prepare the opposed surfaces of the cuneiforms defining the intercuneiform joint and apply one or more fixation devices across the joint to promote fusion. Alternatively, the clinician may prepare one or both cuneiforms for fusion before performing any or all of the steps of the metatarsal correction process and/or apply the one or more fixation devices across the intermediate cuneiform joint before performing any or all of the steps of the metatarsal correction process.

Figure 10:
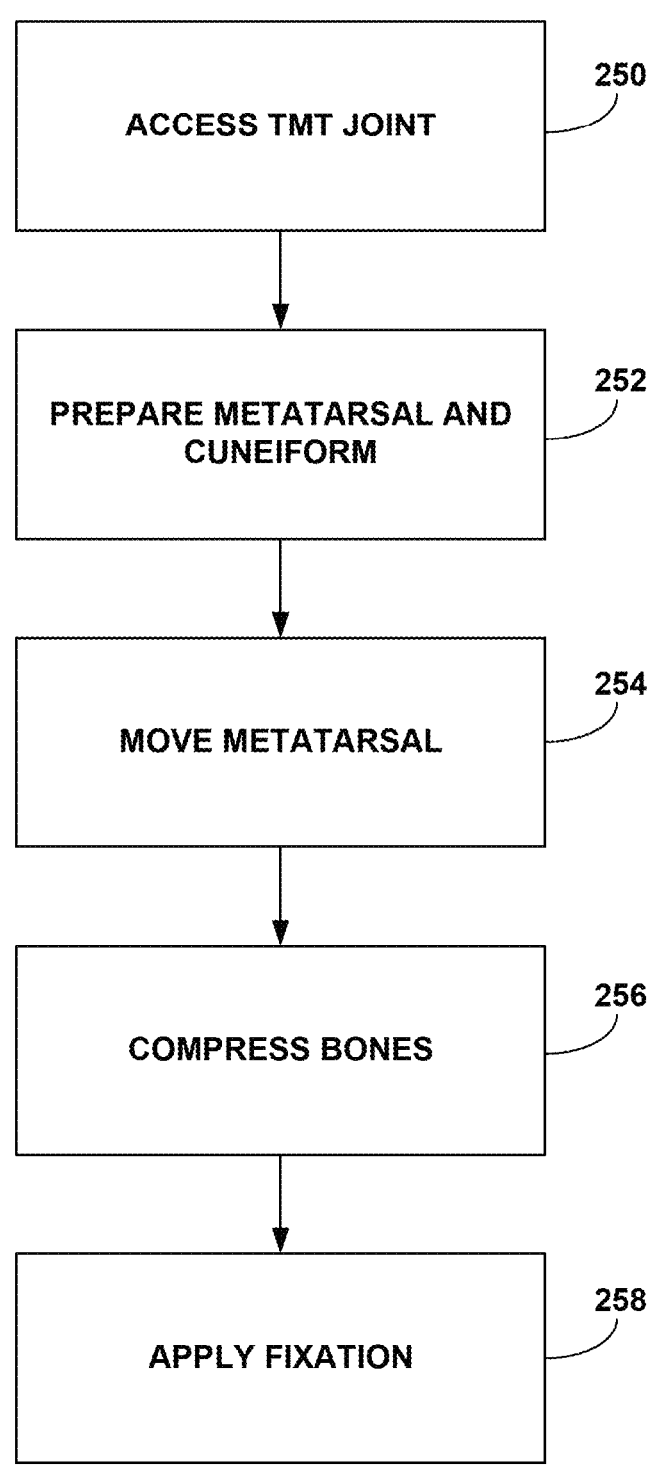
FIG. 10 is a flow diagram of an example technique for performing a metatarsal correction that may performed in conjunction with preparation and fixation of an intercuneiform joint.

FIG. 10 is a flow diagram of an example technique for performing a metatarsal correction that may performed in conjunction with preparation and fixation of an intercuneiform joint. Additional details on example surgical techniques that can be used, including example instrumentation that can be used during the techniques, can be found in U.S. Pat. No. 9,622,805, issued Apr. 18, 2017 and entitled "BONE POSITIONING AND PREPARING GUIDE SYSTEMS AND METHODS" and US Patent Publication No. 2020/0015856, published Jan. 16, 2020 and entitled "COMPRESSOR-DISTRACTOR FOR ANGULARLY REALIGNING BONE PORTIONS," the entire contents of each of which are incorporated herein by reference.

In the example of FIG. 10, the method includes at step 250 making an incision to access the TMT joint. The incision can be made through the skin, such as on a dorsal side of the foot, a medial side of the foot, or on a dorsal-medial side of the foot. The incision can be made to provide surgical access to the TMT joint 126 which separates first metatarsal 102 from opposed medial cuneiform 118. To surgically access the joint, the patient may be placed in a supine position on the operating room table and general anesthesia or monitored anesthesia care administered. Hemostasis can be obtained by applying thigh tourniquet or mid-calf tourniquet. In some examples, imaging of the foot can be used to assist the clinician in ascertaining the location of TMT joint 126 about which incision can be centered when subsequently cutting through skin.

At step 252, the example method includes preparing first metatarsal 102 and/or medial cuneiform 118 for fusion. With the TMT joint 126 exposed via the incision, an end face (e.g., proximal end face) of first metatarsal 102 and/or an end face (e.g., distal end face) of medial cuneiform 118 can be prepared. It is to be noted that one or both of the end faces of the metatarsal and the cuneiform can be prepared before and/or after the metatarsal is moved relative to the cuneiform in one or more planes. Accordingly, unless otherwise specified, the order of bone preparation and/or movement is not limited.

In general, the clinician can prepare the end of each bone forming TMT joint 126 so as to promote fusion of the bone ends across the TMT joint following realignment. Bone preparation may involve using a tissue removing instrument to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand or with the aid of a cutting guide having a guide surface positionable over the portion of bone to be cut. When using a bone preparation guide, a cutting instrument can be inserted against a guide surface (e.g., between a slot define between two guide surfaces) of the bone preparation guide to guide the cutting instrument for bone removal.

The example method of FIG. 10 includes at step 254 moving first metatarsal 102. As noted, first metatarsal 102 can be moved before and/or after first metatarsal 102 and/or medial cuneiform 118 are prepared. Moving first metatarsal 102 can include moving the first metatarsal in at least one plane. For example, first metatarsal 102 can be moved in at least a transverse plane to close the IMA between first metatarsal 102 and adjacent second metatarsal 104 and/or a frontal plane (e.g., to reposition the sesamoid bones substantially centered under the metatarsal). In some examples, first metatarsal 102 can be moved in multiple planes, such as the transverse plane and/or frontal plane and/or sagittal plane (e.g., each of the transverse, frontal, and sagittal planes). The clinician may or may not utilize a bone positioning device to facilitate movement of the bone portion. The moved position of first metatarsal 102 can result is realignment of first metatarsal 102 relative to one of more other adjacent bones.

The example method of FIG. 10 may include at step 254 compressing one or more bones. In some applications, this compression step may be omitted depending on the realigned position of the first metatarsal 102. When included, the prepared end faces of the bone portions of first metatarsal 102 and medial cuneiform 118 can be compressed together prior to fixating the position of these bones. The clinician may compress the end faces together with hand pressure and/or using a compressing instrument physically attached to both the two bones.

The method of FIG. 10 includes at step 256 apply an implant to the first metatarsal 102 and to the medial cuneiform 118 across TMT joint 126 separating the two bones. Example metatarsal implants that can be used include one or more plates, staples, screws, pins, and combinations thereof.

Various examples have been described. These and other examples are within the scope of the following claims.

The invention claimed is:

1. A method of preparing an intercuneiform joint for fusion, the method comprising:

inserting an orthopedic rasp into an intercuneiform joint between a first cuneiform and a second cuneiform, the orthopedic rasp comprising a body defining a first widthwise surface and a second widthwise surface opposite the first widthwise surface and a rasp head defined along a portion of a length of the body, the rasp head comprising a plurality of cutting teeth extending outwardly from one or both of the first widthwise surface and the second widthwise surface of the body;

manually moving the orthopedic rasp relative to the first cuneiform and the second cuneiform, thereby causing the plurality of cutting teeth to prepare a surface of the first cuneiform and to prepare an opposed surface of the second cuneiform across the intercuneiform joint; and applying a fixation device to the first cuneiform and the second cuneiform and across the intercuneiform joint, the fixation device holding the surface of the first cuneiform prepared by the plurality of cutting teeth in contact with the opposed surface of the second cuneiform prepared by the plurality of cutting teeth for fusion.

2. The method of claim 1, wherein the rasp head has a thickness within a range from 0.8 mm to 1.8 mm, the rasp head defines a width within a range from 4 mm to 6 mm, and the rasp head defines a length within a range from 15 mm to 30 mm.

3. The method of claim 1, wherein:

the plurality of cutting teeth comprise a first plurality of cutting teeth extending outwardly from the first widthwise surface of the body and a second first plurality of cutting teeth extending outwardly from the second widthwise surface of the body;

manually moving the orthopedic rasp relative to the first cuneiform and the second cuneiform comprises causing the first plurality of cutting teeth to prepare the surface of the first cuneiform and the second plurality of cutting teeth to prepare the opposed surface of the second cuneiform; and applying the fixation device to the first cuneiform and the second cuneiform and across the intercuneiform joint comprises applying the fixation device holding the surface of the first cuneiform prepared by the first plurality of cutting teeth in contact with the opposed surface of the second cuneiform prepared by the second plurality of cutting teeth for fusion.

4. The method of claim 1, wherein moving the orthopedic rasp relative to the first cuneiform and the second cuneiform comprises simultaneously causing the first plurality of cutting teeth of prepare the surface of the first cuneiform and the second plurality of cutting teeth of prepare the opposed surface of the second cuneiform.

5. The method of claim 1, wherein:

the plurality of cutting teeth extend outwardly from the first widthwise surface of the body;

the second widthwise surface of the body is devoid of cutting teeth; and manually moving the orthopedic rasp relative to the first cuneiform and the second cuneiform comprises applying the plurality of cutting teeth to prepare the surface of the first cuneiform and then flipping the body over to apply the plurality of cutting teeth to prepare the opposed surface of the second cuneiform.

6. The method of claim 1, wherein inserting the orthopedic rasp into the intercuneiform joint comprises inserting the orthopedic rasp plantarly into the intercuneiform joint to a depth indicated by a depth marking on the body.

7. The method of claim 1, wherein manually moving the orthopedic rasp relative to the first cuneiform and the second cuneiform comprises reciprocating the orthopedic rasp dorsally and plantarly.

8. The method of claim 1, wherein the orthopedic rasp comprises a handle configured to be manually grasped by a user, and inserting the orthopedic rasp into the intercuneiform joint and manually moving the orthopedic rasp relative to the first cuneiform and the second cuneiform comprises inserting the orthopedic rasp and manually moving the orthopedic rasp via hand movement of the user grasping the handle.

9. The method of claim 1, wherein applying the fixation device across the first cuneiform and the second cuneiform comprises inserting the fixation device through the intercuneiform joint space.

10. The method of claim 9, wherein inserting the fixation device through the intercuneiform joint space comprises inserting the fixation device through the surface of the first cuneiform prepared by the plurality of cutting teeth and through the opposed surface of the second cuneiform prepared by the plurality of cutting teeth.

11. The method of claim 1, wherein at least some of the plurality of cutting teeth are spaced apart from each other widthwise across one or both of the first widthwise surface and the second widthwise surface.

12. The method of claim 11, wherein:
 a widthwise spacing between adjacent pairs of the plurality of cutting teeth is within a range from 0.3 mm to 0.7 mm; and
 a lengthwise spacing between adjacent pairs of the plurality of cutting teeth is within a range from 0.5 mm to 1.5 mm.

13. The method of claim 1, wherein each of the plurality of cutting teeth are configured as a unidirectional cutting tooth having a cutting surface facing a proximal end of the body.

14. The method of claim 13, wherein each of the plurality of cutting teeth comprises:
 a tapered leading surface extending from the first widthwise surface or the second widthwise surface outwardly in a direction tapered toward the proximal end; and
 a trailing cutting surface extending from the first widthwise surface or the second widthwise surface, the trailing cutting surface joining the tapered leading surface.

15. The method of claim 1, wherein the body defines a first leading surface extending angularly outwardly from a distal end of the body and a second leading surface extending angularly outwardly from the distal end of the body in an opposite direction from the first leading surface.

16. The method of claim 1, wherein the first widthwise surface and the second widthwise surface are each planar surfaces.

17. The method of claim 1, further comprising:
 moving a metatarsal separated from the first cuneiform across a tarsometatarsal joint in at least a transverse plane to close an intermetatarsal angle between the metatarsal and an adjacent metatarsal;
 preparing an end of the metatarsal for fusion;
 preparing an end of the first cuneiform facing the metatarsal for fusion; and
 applying a metatarsal fixation device to the metatarsal and the first cuneiform and across the tarsometatarsal joint.

18. The method of claim 17, wherein applying the metatarsal fixation device to the metatarsal and the first cuneiform comprises applying the metatarsal fixation device prior to applying the fixation device to the first cuneiform and the second cuneiform.

\* \* \* \* \*